(12) United States Patent
Lechler et al.

(10) Patent No.: US 9,090,708 B2
(45) Date of Patent: *Jul. 28, 2015

(54) PORCINE CTLA-4 FOR XENOGRAFT-SPECIFIC IMMUNOSUPPRESSION

(75) Inventors: Robert Ian Lechler, London (GB); Anthony Dorling, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,791

(22) Filed: Dec. 12, 2011

(65) Prior Publication Data
US 2013/0078266 A1   Mar. 28, 2013

Related U.S. Application Data

(63) Continuation of application No. 12/231,608, filed on Sep. 4, 2008, now Pat. No. 8,097,598, which is a continuation of application No. 09/674,462, filed as application No. PCT/GB99/01350 on Apr. 30, 1999, now Pat. No. 7,432,344.

(30) Foreign Application Priority Data

Apr. 30, 1998  (GB) .................................. 9809280.2

(51) Int. Cl.
| | |
|---|---|
| C07K 14/70 | (2006.01) |
| A01K 67/02 | (2006.01) |
| A61K 39/00 | (2006.01) |
| C07K 16/28 | (2006.01) |
| C07K 14/705 | (2006.01) |
| A01K 67/027 | (2006.01) |
| A61K 38/00 | (2006.01) |
| A61K 48/00 | (2006.01) |

(52) U.S. Cl.
CPC ....... *C07K 14/70596* (2013.01); *A01K 67/0275* (2013.01); *A61K 39/001* (2013.01); *C07K 14/70521* (2013.01); *C07K 14/70532* (2013.01); *C07K 16/2818* (2013.01); *A01K 2217/05* (2013.01); *A61K 38/00* (2013.01); *A61K 48/00* (2013.01); *A61K 2039/5154* (2013.01); *A61K 2039/5156* (2013.01); *C07K 2317/622* (2013.01); *C07K 2319/00* (2013.01); *C07K 2319/30* (2013.01)

(58) Field of Classification Search
None
See application file for complete search history.

(56) References Cited

U.S. PATENT DOCUMENTS 8,097,598 B2 *  1/2012  Lechler et al. ............. 514/44 R

* cited by examiner

*Primary Examiner* — Ilia Ouspenski
(74) *Attorney, Agent, or Firm* — King & Spalding LLP

(57) ABSTRACT

The invention provides methods for inhibiting T-cell mediated rejection of a xenotransplanted organ by blocking the delivery of co-stimulatory signal 2 (the B7/CD28 interaction) prevent the activation of xenoreactive T-cells in the recipient. In a first aspect, co-stimulation is prevented by administration to the organ recipient of a soluble form of CTLA-4 from the xenogeneic donor organism. In a second aspect, co-stimulation is antagonized by expressing a ligand for CTLA-4 on the xenogeneic donor cells. In a third aspect, co-stimulation is prevented by expressing recipient organism MHC class II on the surface of the cells of the xenogeneic donor organ.

14 Claims, 18 Drawing Sheets

FIG. 2

```
         -30         -20         -10          1           11          21
MACSGFRSHG  AWLELTSRTW  PCTALFSLLF  IPVFSKGMHV  AQPAVVLANS  RGVASFVCEY   SEQ ID:1 (pCTLA4)
···L··QR·K  ·Q·N·AA···  ···L··F···  ····C·A···  ······S···  ··I·······  Human CTLA4
·····Q····  T·W--·····  ······F·V·  ········N·  T··P·····S  ······S···  Cattle CTLA4
                                         *
          31          41          51          61          71          81
GSAGKAAEVR  VTVLRRAGSQ  MTEVCAATYT  VEDELTFLDD  STCTGTSTEN  KVNLTIQGLR
A·P···T···  ·····Q·D··  V·········  ···MGN····  ·I····SG··  Q·········
E·S···D···  ·····E····  V·····G··M  ··········  ··I···RG··  ··········

91         101         111         121         131         141
AVDTGLYICK  VELLYPPPYY  VGMGNGTQIY  VIDPEPCPDS  DFLLWILAAV  SSGLFFYSFL
·M········  ···MYPPPYY  L·I···A···  ··········  ··········  ··········
·M····V···  ···MYPPPYY  ··I·······  ··········  ··········  ··········
                                                    *

151         161         171         181
ITAVSLSKML  KKRSPLTTGV  YVKMPPTEPE  CEKQFQPYFI  PIN
L·········  ··········  ··········  ··········  ···
··········  ··········  ··········  ··········  ···
     *
```

FIG. 3

```
1                11              21              31              41              51
ATGGCTTGCT       CTGGATTCCG      GAGCCATGGG      GCTTGGCTGG      AGCTTACTTC      TAGGACCTGG
.........C       T.....T.A       .C.G..CAA.      ...CA....A      .C..GG..G.      C.........
.........        .........       ........        A.......        .-----.A..      ..........
                                                                       *

61               71              81              91              101             111
CCCTGTACAG       CTCTGTTTTC      TCTTCTCTTC      ATCCCTGTCT      TCTCCAAAGG      GATGCACGTG
....C..TC        TC......T       ........        ........        ...G....C       A.........
....C..T.        .C..A....T      ....G....       ......T..       ....T.....      ...A.T....
                                                                                       +

121              131             141             151             161             171
GCCCAACCTG       CAGTAGTGCT      GGCCAACAGC      CGGGGTGTTG      CCAGCTTTGT      GTGTGAGTAT
.....G....       .T.G..A..       .....G....      ..A..CA.C.      ..........      ..........
A.....G...       .....G....      ...T.G....      ..........      ......CTC       A......A..
      §          §

181              191             201             211             221             231
GGGTCTGCAG       GCAAAGCTGC      CGAGGTCCGG      GTGACAGTGC      TGCGGCGGGC      CGGCAGCCAG
.CA...C...       .........       CA..T.....      ..........      ..T....A...     T.A.......
A.....T...       .........A      ..........      ..........      ....GA....      A.........

241              251             261             271             281             291
ATGACTGAAG       TCTGTGCCGC      GACATATACT      GTGGAGGATG      AGTTGACCTT      CCTTGATGAC
G.....C...       ......G..       A..C..C.TG      A...G.A...      ..........      ...A.....T
G....C....       ......T.G       ...C..C.TG      ..........      ...C..A...      ...G.....T 301              311             321             331             341             351
TCTACATGCA       CTGGCACCTC      CACCGAAAAC      AAAGTGAACC      TCACCATCCA      AGGGCTGAGA
..C.TC....       .G.......       ..GT.G...T      C.........      ....T.....      ...A.....G
```

```
361        371        381        391        401        411
GCCGTGGACA CTGGGCTCTA CATCTGCAAG GTGGAGCTCC TGTACCCACC ACCCTACTAT
...A...... .G..A..... .......... .......... .......... G..A.....C
...A...... .......... TG.......A .........A .......G.. G........C 421        431        441        451        461        471
GTGGGTATGG GCAACGGGAC CCAGATTTAT GTCATTGATC CAGAACCATG CCCAGATTCT
C....C..A. ......AG.. .......... ..A....... ......G... ..........
....C..C.. ...T..A.. .......... C......... .......... ..G.......

481        491        501        511        521        531
GATTTCCTGC TCTGGATCCT GGCAGCAGTT AGTTCAGGGT TGTTTTTTTA CAGCTTCCTC
..C....C.. .......... T......... .....G.... .......... T....T....
....T..C.. .......... .......... .......... ....C..... ..........

541        551        561        571        581        591
ATCACAGCTG TTTCTTTGAG CAAAATGCTA AAGAAAAGAA GTCCTCTTAC TACAGGGGTC
C......... .......... .......... .......... ..C....... A.........
.......... .......... .......+.. .......... ..C....... ..........

601        611        621        631        641        651
TATGTGAAAA TGCCCCCGAC AGAGCCAGAA TGTGAAAAGC AATTTCAGCC TTATTTTATT
.......... ......A... .......... .......... .......... ..........
.......... ......A... .......... .......... .......... ..........

661        671
CCCATCAATT GA
.......... ..
.......... ..

SEQ ID: 2 (pCTLA4)
Human CTLA4
Cattle CTLA4
```

```
        -30         -20         -10          1          11          21
MACSGFRSHG  AWLELTSRTW  PCTALFSLLF  IPVFSKGMHV  AQPAVVLANS  RGVASFVCEY 31          41          51          61          71          81
GSAGKAAEVR  VTVLRRAGSQ  MTEVCAATYT  VEDELTFLDD  STCTGTSTEN  KVNLTIQGLR 91         101         111         121         131         141
AVDTGLYICK  VELLYPPPYY  VGMGNGTQIY  VIDPEPCPDS  DGGSGGAAEP  KSCDKTHTCP 151         161         171         181         191         201
PCPAPELLGG  PSVFLFPPKP  KDTLMISRTP  EVTCVVVDVS  HEDPEVKFNW  YVDGVEVHNA 211         221         231         241         251         261
KTKPREEQYN  STYRVVSVLT  VLHQDWLNGK  EYKCKVSNKA  LPAPIEKTIS  KAKGQPREPQ 271         281         291         301         311         321
VYTLPPSRDE  LTKNQVSLTC  LVKGFYPSDI  AVEWESNGQP  ENNYKTTPPV  LDSDGSFFLY 331         341         351         361
SKLTVDKSRW  QQGNVFSCSV  MHEALHNHYT  QKSLSLSPGK
```

FIG. 8

```
1.........  11.........  21.........  31.........  41.........  51.........  61.........  71.........
CCGAGGTGCA  GCTGGTGGAG   TCTGGGGGAG   GCTTGGTACA   GCCTGGGGGG   TCCCTGAGAC   TCTCCCTGTGC  AGCCTCTGGA

81.........  91.........  101........  111........  121........  131........  141........  151........
TTCACCTTTA   GCAGCTATGC   CATGAGCTGG   GTCCGCCAGG   CTCCAGGGAA   GGGGCTGGAG   TGGGTCTCAG   CTATTAGTGG

161........  171........  181........  191........  201........  211........  221........  231........
TAGTGGTGGT   AGCACATACT   ACGCAGACTC   CGTGAAGGGC   CGGTTCACCA   TCTCCAGAGA   CAATTCCAAG   AACACGCTGT

241........  251........  261........  271........  281........  291........  301........  311........
ATCTGCAAAT   GAACAGCCTG   AGAGCCGAGG   ACACGGCCGT   GTATTACTGT   GCAAGAGCTG   GTCGTATTTT   GTTTGACTAT

321........  331........  341........  351........  361........  371........  381........  391........
TGGGGCCAAG   GTACCCTGGT   CACCGTCTCG   AGTGGTGGAG   GCGGTTCAGG   CGGAGGTGGC   TCTGGCGGTA   GTGCACTTCA

401........  411........  421........  431........  441........  451........  461........  471........
GTCTGTGCTG   ACTCAGCCAC   CCTCAGCGTC   TGGGACCCCC   GGGCAGAGGG   TCACCATCTC   TTGTTCTGGA   AGCAGCTCCA

481........  491........  501........  511........  521........  531........  541........  551........
ACATCGGAAG   TAATTATGTA   TACTGGTACC   AGCAGCTCCC   AGGAACGGCC   CCCAAACTCC   TCATCTATAG   GAATAATCAG

561........  571........  581........  591........  601........  611........  621........  631........
CGGCCCCTCAG  GGGTCCCTGA  CCGATTCTCT   GGCTCCAAGT   CTGGCACCTC   AGCCTCCCTG   GCCATCAGTG   GGCTCCGGTC

641........  651........  661........  671........  681........  691........  701........  711........
CGAGGATGAG   GCTGATTATT   ACTGTGCAGC   ATGGGATGAC   AGCCTGGTAT   TCGGCGGAGG   GACCAAGCTG   ACCGTCCTAG

721
GT
```

```
1.......... 11.......... 21.......... 31.......... 41.......... 51.......... 61.......... 71..........
EVQLVESGGG LVQPGGSLRL SCAASGFTFS SYAMSWVRQA PGKGLEWVSA ISGSGGSTYY ADSVKGRFTI SRDNSKNTLY

81.......... 91.......... 101......... 111......... 121......... 131......... 141......... 151.........
LQMNSLRAED TAVYYCARAG RILFDYWGQG TLVTVSSGGG GSGGGGSGGG GSGGGGSGGS ALQSVLTQPP SASGTPGQRV TISCSGSSSN
                                          LINKER

161......... 171......... 181......... 191......... 201......... 211......... 221......... 231.........
IGSNYVYWYQ QLPGTAPKLL IYRNNQRPSG VPDRFSGSKS GTSASLAISG LRSEDEADYY CAAWDDSLVF GGGTKLTVLG
```

FIG. 10

```
              10        20        30        40        50        60
              |         |         |         |         |         |
M1  sFv   CATGG-CCGAGGTGCAGCTGGTGGAGTCTGGGGGAGGCTTGGTACAGCCTGGGGGGTCCCTGAG
M3  sFv   CATGG-CCCAGGTGCAGCTGCAGGAGTCGGGCCCAGGACTGGTGAAGCCTTCGGAGACCCTGTC
M19 sFv   CATGG-CCCAGGTGCAGCTGGTGCAGTCTGGGGCTGAGGTGAAGAGGCCTGGGGCCTCAGTGAA
M24 sFv   CATGGGCCCAGGTGCAGCTGTTGCAGTCTGCAGCAGAGGTGAAAAAGCCCGGGGAGTCTCTGAA 70        80        90       100       110       120
              |         |         |         |         |         |
M1  sFv   ACTCTCCTGTGCAGCCTCTGGATTCACCTTTAGCAGC--TA--TGCCAT--GAGCTGGGTCCGC
M3  sFv   CCTCACCTGCACTGTCTCTGGTGGCTCCGTCAGCAGTGGTAGTTACTACTGGAGCTGGATCCGG
M19 sFv   GGTTTCCTGCAAGGCATCTGGATACACCTTCACCAGC------TACTATATGCACTGGGTGCGA
M24 sFv   GATCTCCTGTAAGGGTTCTGGATACAGCTTTACCAGC------TACTGGATCGGCTGGGTGCGC 130       140       150       160       170       180       190
              |         |         |         |         |         |         |
M1  sFv   CAGGCTCCAGGGAAGGGGCTGGAGTGGGTCTCAGCTATTAGTGGTAGTGGTGGTAGCACATACT
M3  sFv   CAGCCCCCAGGGAAGGGACTGGAGTGGATT--GGGTAT-ATCTATTACAGTGGGAGCACCAACT
M19 sFv   CAGGCCCCTGGACAAGGGCTTGAGTGGATGGGAATAATCAACCCTAGTGGTGGTAGCACAAGCT
M24 sFv   CAGATGCCCGGGAAAGGCCTGGAGTGGATGGGGATCATCTATCCTGGTGACTCTGATACCAGAT 200       210       220       230       240       250
              |         |         |         |         |         |
M1  sFv   ACGCAGACTCCGTGAAGGGCCGGTTCACCATCTCCAGAGACAATTCCAAGAACACGCTGTATCT
M3  sFv   ACAACCCCTCCCTCAAGAGTCGAGTCACCATATCAGTAGACACGTCCAAGAACCAGTTCTCCCT
M19 sFv   ACGCACAGAAGTTCCAGGGCAGAGTCACCATGACCAGGGACACGTCCACGAGCACAGTCTACAT
M24 sFv   ACAGCCCGTCCTTCCAAGGCCAGGTCACCATCTCAGCCGACAAGTCCATCAGCACCGCCTACCT 260       270       280       290       300       310       320
              |         |         |         |         |         |         |
M1  sFv   GCAAATGAACAGCCTGAGAGCCGAGGACACGGCCGTGTATTACTGTGCAAGAGCTG------GT
M3  sFv   GAAGCTGAGCTCTGTGACCGCTGCGGACACGGCCGTGTATTACTGTGCAAGAATGC------GG
M19 sFv   GGAGCTGAGCAGCCTGAGATCTGAGGACACGGCCGTGTATTACTGTGCAAGAGTGGCTCCCTAT
M24 sFv   GCAGTGGAGCAGCCTGAAGGCCTCGGACACGGCCGTGTATTACTGTCAAGATT--TTCGCT-T 330       340       350       360       370       380
              |         |         |         |         |         |
M1  sFv   CGTATTTTGTTTGACTATTGGGGCCAAGGTACCCTGGTCACCGTCTCGAGTGGTGGAGGCGGTT
M3  sFv   AAGGATAAGTTTGACTATTGGGGCCAAGGTACCCTGGTCACCGTCTCGAGTGGTGGAGGCGGTT
M19 sFv   GTGAATACGCTTGTTTTTTGGGGCCAAGGTACCCTGGTCACCGTCTCGAGTGGTGGAGGCGGTT
M24 sFv   GGTGGT---TTTGACTATTGGGGCCAAGGTACCCTGGTCACCGTCTCGAGTGGTGGAGGCGGTT
```

```
                        390       400       410       420       430       440
                         |         |         |         |         |         |
M1  sFv    CAGGCGGAGGTGGCTCTGGCGGTAGTGCACTTCAGTCTGTGCTGACTCAG---CCACCCTCAGC
M3  sFv    CAGGCGGAGGTGGCTCTGGCGGTAGTGCACTTCAGTCTGTGCTGACTCAG---CCACCCTCAGC
M19 sFv    CAGGCGGAGGTGGCTCTGGCGGTAGTGCACTTTCTTCTGAGCTGACTCAG---GACCCTGCTGT
M24 sFv    CAGGCGGAGGTGGCTCTGGCGGTAGTGCACTTGACATCCAGTTGACCCAGTCTCCATCCTTCCT 450       460       470       480       490       500       510
               |         |         |         |         |         |         |
M1  sFv    GTCTGGGACCCCCGGGCAGAGGGTCACCATCTCTTGTTCTGGAAGCAGCTCCAACATCGGAAGT
M3  sFv    GTCTGGGACCCCCGGGCAGAGGGTCACCATCTCTTGTTCTGGAAGCAGCTCCAACATCGGAAGT
M19 sFv    GTCTGTGGCCTTGGGACAGACAGTCAGGATCACATGCCAAGGAGACAGCCTCA------GAAGC
M24 sFv    GTCTGCATCTGTAGGAGACAGAGTCACCATCACTTGCC---GGGCCAGTCAGGGCATT---AGC 520       530       540       550       560       570
                  |         |         |         |         |         |
M1  sFv    AATTATGTATACTGGTACCAGCAGCTCCCAGGAACGGCCCCCAAACTCCTCATCTATAGGAATA
M3  sFv    AATTATGTATACTGGTACCAGCAGCTCCCAGGAACGGCCCCCAAACTCCTCATCTATAGGAATA
M19 sFv    TATTATGCAAGCTGGTACCAGCAGAAGCCAGGACAGGCCCCTGTACTTGTCATCTATGGTAAAA
M24 sFv    AGTTATTTAGCCTGGTATCAGCAAAAACCAGGGAAAGCCCCTAAGCTCCTGGTCTATGCTGCAT 580       590       600       610       620       630       640
               |         |         |         |         |         |         |
M1  sFv    ATCAGCGGCCCTCAGGGGTCCCTGACCGATTCTCTGGCTCCAAGTCTGGCACCTCAGCCTCCCT
M3  sFv    ATCAGCGGCCCTCAGGGGTCCCTGACCGATTCTCTGGCTCCAAGTCTGGCACCTCAGCCTCCCT
M19 sFv    ACAACCGGCCCTCAGGGATCCCAGACCGATTCTCTGGCTCCAGCTCAGGAAACACAGCTTCCTT
M24 sFv    CCACTTTGCAAAGTGGGGTCCCATCAAGGTTCAGCGGCAGTGGATCTGGGACAGAATTCACTCT 650       660       670       680       690       700
                  |         |         |         |         |         |
M1  sFv    GGCCATCAGTGGGCTCCGGTCCGAGGATGAGGCTGATTATTACTGTGCAGCATGGGATGACAGC
M3  sFv    GGCCATCAGTGGGCTCCGGTCCGAGGATGAGGCTGATTATTACTGTGCAGCATGGGATGACAGC
M19 sFv    GACCATCACTGGGCTCAGGCGGAAGATGAGGCTGACTATTACTGTAACTCCCGGGACAGCAGT
M24 sFv    CACCAATCAGCAGCCTGCAGCCTGAAGATTTTGCAACTTATTACTGTCA---ACAGCTTAATAGT 710       720       730       740       750
                  |         |         |         |         |
M1  sFv    --CTG----GTATTCGGCGGAGGGACCAAGCTGACCGTCCTAGGTGC
M3  sFv    --CTGT-TTGTATTCGGCGGAGGGACCAAGCTGACCGTCCTAGGTGCGGCCGC
M19 sFv    GGTTTTACTGTATTCGGCGGAGGGACCAAGCTGACCGTCCTAGGTGC
M24 sFv    TACCGCTTGACGTTCGGCCAAGGGACCAAGCTGGAAATC--AAACGTG----C
```

```
                    10        20        30        40        50        60
                    |         |         |         |         |         |
                |····|·||  | |·| ||  ||·  ··   |   ··  ·|··  ··|····||  ·   ||
M1  sFv Peptide   --EVQLVESGGGLVQPGGSLRLSCAASG--FTFSSYAMSWVRQAPGKGLEWVSAISGSGG
M3  sFv Peptide   MAQVQLQESGPGLVKPSETLSLTCTVSGGSVSSGSYYWSWIRQPPGKGLEWIGYIY-YSG
M19 sFv Peptide   --QVQLVQSGAEVKRPGASVKVSCKASG--YTFTSYYMHWVRQAPGQGLEWMGIINPSGG
M24 sFv peptide   --QVQLLQSAAEVKKPGESLKISCKGSG--YSFTSYWIGWVRQMPGKGLEWMGIIYPGDS 70        80        90       100       110       120
                    |         |         |         |         |         |
                ·· ·   |||·||·· · |   |||·|  |  ·········    |   |········
M1  sFv Peptide   STYYADSVKGRFTISRDNSKNTLYLQMNSLRAEDTAVYYCARAGR--ILFDYWGQGTLVT
M3  sFv Peptide   STNYNPSLKSRVTISVDTSKNQFSLKLSSVTAADTAVYYCARMRK--IKFDYWGQGTLVT
M19 sFv Peptide   STSYAQKFQGRVTMTRDTSTSTVYMELSSLRSEDTAVYYCARVAPYVNTLVFWGQGTLVT
M24 sFv Peptide   DIRYSPSFQGQVTISADKSISTAYLQWSSLKASDTAVYYCARFS--LGGFDYWGQGTLVT 130       140       150       160       170       180
                    |         |         |         |         |         |
                ················   ····|  ·  ·|··|· |        ·· ····· ·
M1  sFv Peptide   VSSGGGGSGGGGSGGGSALQSVLTQPPS-ASGTPGQRVTISCSGSSSNIGSNYVYWYQQLP
M3  sFv Peptide   VSSGGGGSGGGGSGGGSALQSVLTQPPS-ASGTPGQRVTISCSGSSSNIGSNYVYWYQQLP
M19 sFv Peptide   VSSGGGGSGGGGSGGGSALSSELTQDPA-VSVALGQTVRITCQGDS--LRSYYASWYQQKP
M24 sFv peptide   VSSGGGGSGGGGSGGGSALDIQLTQSPSFLSASVGDRVTTTCRASQG--ISSYLAWYQQKP 190       200       210       220       230       240
                    |         |         |         |         |         |
                · ··· ·||·  |   ··|·  ······ ··    |·|·|| ||··  ·····    ··
M1  sFv Peptide   GTAPKLLIYRNNQRPSGVPDRFSGSKSGTSASLAISGLRSEDEADYYCAAWDDSL--VFG
M3  sFv Peptide   GTAPKLLIYRNNQRPSGVPDRFSGSKSGTSASLAISGLRSEDEADYYCAAWDDSLP-VFG
M19 sFv Peptide   GQAPVLVIYGKNNRPSGIPDRFSGSSSGNTASLTTTGAQAEDEADYYCNSRDSSGPTVFG
M24 sFv peptide   GKAPKLLVYAASTLQSGVPSRFSGSGSGTEFTLTISSLQPEDFATYYCQQLNSYRLT-FG ····|
M1  sFv Peptide   GGTKLTVLG
M3  sFv Peptide   GGTKLTVLGAA
M19 sFv Peptide   GGTKLTVLG
M24 sFv peptide   QGTKLEI--KR
```

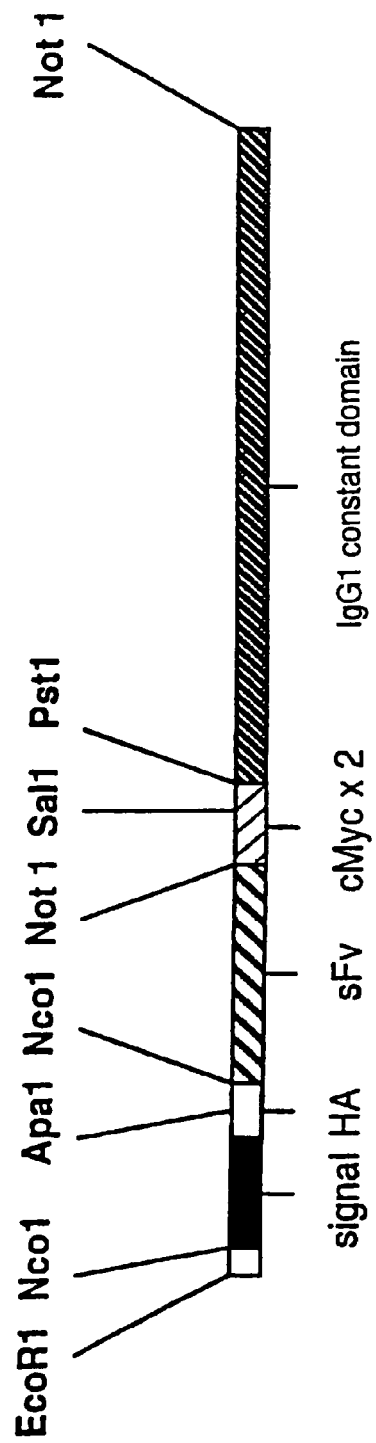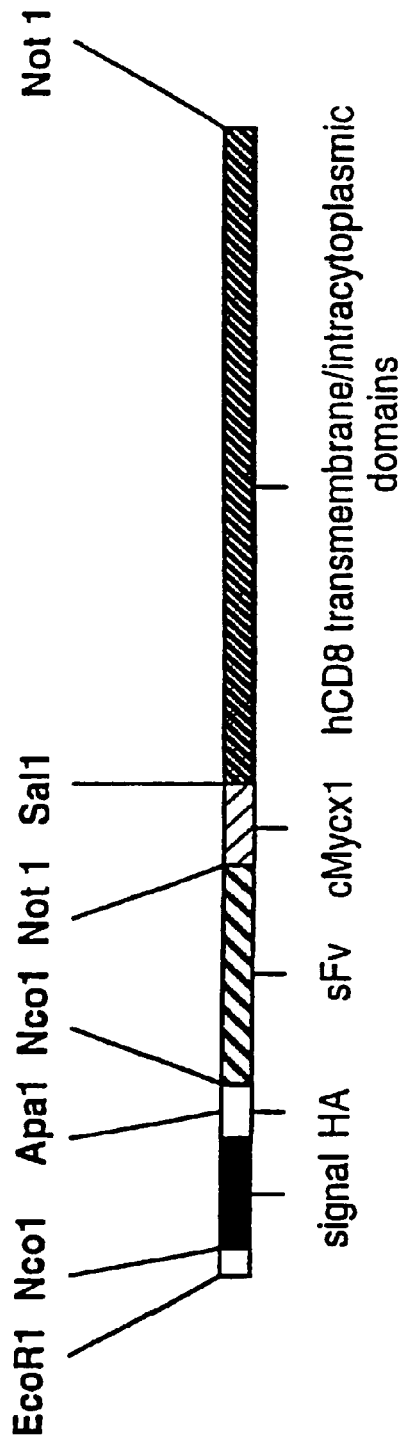

FIG. 15(A)

```
 -65  AGCTTCAGGA TCCTGAAAGG TTTTGCTCTA CTTCCTGAAG ACCTGAACAC
 -15  CGCTCCCATA AAGCCATGGC TTGCCTTGGA TTTCAGCGGC ACAAGGCTCA
  36  GCTGAACCTG GCTACCAGGA CCTGGCCCTG CACTCTCCTG TTTTTTCTTC
  86  TCTTCATCCC TGTCTTCTGC AAAGCAATGC ACGTGGCCCA GCCTGCTGTG
 136  GTACTGGCCA GCAGCCGAGG CATCGCCAGC TTTGTGTGTG AGTATGCATC
 186  TCCAGGCAAA GCCACTGAGG TCCGGGTGAC AGTGCTTCGG CAGGCTGACA
 236  GCCAGGTGAC TGAAGTCTGT GCGGCAACCT ACATGATGGG GAATGAGTTG
 286  ACCTTCCTAG ATGATTCCAT CTGCACGGGC ACCTCCAGTG GAAATCAAGT
 336  GAACCTCACT ATCCAAGGAC TGAGGGCCAT GGACACGGGA CTCTACATCT
 386  GCAAGGTGGA GCTCATGTAC CCACCGCCAT ACTACCTGGG CATAGGCAAC
 436  GGAACCCAGA TTTATGTAAT TGATCCAGAA CCGTGCCCAG ATTCTGACTT
 486  CCTCCTCTGG ATCCTTGCAG CAGTTAGTTC GGGGTTGTTT TTTTATAGCT
 536  TTCTCCTCAC AGCTGTTTCT TTGAGCAAAA TGCTAAAGAA AAGAAGCCCT
 586  CTTACAACAG GGGTCTATGT GAAAATGCCC CCAACAGAGC CAGAATGTGA
 636  AAAGCAATTT CAGCCTTATT TTATTCCCAT CAATTGAGAA TT
```

FIG. 15(B)

```
         -30        -20        -10          1         11         21
      MACLGFQRHK AQLNLATRTW PCTLLFFLLF IPVFCKAMHV AQPAVVLASS RGIASFVCEY
                                                *

31         41         51         61         71         81
      ASPGKATEVR VTVLRQADSQ VTEVCAATYM MGNELTFLDD SICTGTSSGN QVNLTIQGLR 91        101        111        121        131        141
      AMDTGLYICK VELMYPPPYY LGIGNGTQIY VIDPEPCPDS DFLLWILAAV SSGLFFYSFL
                                                                   *

151        161        171        181
      LTAVSLSKML KKRSPLTTGV YVKMPPTEPE CEKQFQPYFI PIN
         *
```

FIG. 16

```
-36   AAGCTTCGAG CCAAGCAGCG TCCTGGGGAG CGCGTCATGG CCTTACCAGT
 15   GACCGCCTTG CTCCTGCCGC TGGCCTTGCT GCTCCACGCC GCCAGGCCGA
 65   GCCAGTTCCG GGTGTCGCCG CTGGATCGGA CCTGGAACCT GGGCGAGACA
115   GTGGAGCTGA AGTGCCAGGT GCTGCTGTCC AACCCGACGT CGGGCTGCTC
165   GTGGCTCTTC CAGCCGCGCG GCGCCGCCGC CAGTCCCACC TTCCTCCTAT
215   ACCTCTCCCA AAACAATCCC AAGGCGGCCA AGGGGCTGGA CACCCAGCGG
265   TTCTCGGGCA AGAGGTTGGG GGACACCTTC GTCCTCACCC TGAGCGACTT
315   CCGCCGAGAG AACGAGGGCT ACTATTTCTG CTCGGCCCTG AGCAACTCCA
365   TCATGTACTT CAGCCACTTC GTGCCGGTCT TCCTGCCAGC GAAGCCCACC
415   ACGACGCCAG CGCCGCGACC ACTAACACCG GCGCCCACCA TCGCGTCGCA
465   GCCCCTGTCC CTGCGCCCAG AGGCGTGCCG GCCAGCGGCG GGGGGCGCAG
515   TGCACACGAG GGGGCTGGAC TTCGCCTGTG ATATCTACAT CTGGGCGCCC
565   CTGGCCGGGA CTTGTGGGGT CCTTCTCCTG TCACTGGTTA TCACCCTTTA
615   CTGCAACCAC AGGAACCGAA GACGTGTTTG CAAATGTCCC CGGCCTGTGG
665   TCAAATCGGG AGACAAGCCC AGCCTTTCGG CGAGATACGT CTAACCCTGT
715   GCAACAGCCA CTACATGAAT TCC
```

PORCINE CTLA-4 FOR XENOGRAFT-SPECIFIC IMMUNOSUPPRESSION

This application is a continuation of U.S. application Ser. No. 12/231,608, filed Sep. 4, 2008, which is a continuation of U.S. application Ser. No. 09/674,462, filed May 8, 2001, now U.S. Pat. No. 7,432,344, which claims priority under 35 U.S.C. §371 to PCT Application PCT/GB99/01350, filed Apr. 30, 1999, which claims priority to UK Application GB 9809280.2, filed Apr. 30, 1998, the entire contents of which are incorporated herein by reference. This invention relates to the suppression of xenograft rejection.

BACKGROUND TO THE INVENTION

The success of allogeneic organ transplantation has been established in the last few decades, but the limited supply of donor organs means that many patients have little or no chance of receiving a transplanted organ, such as a kidney, heart or liver. A significant number of these people die whilst awaiting an organ. One potential solution is "xenografting", or the use of organs from a non-human ("xenogeneic") animal donor.

Porcine donor organs are thought to be suitable candidates because pigs are anatomically and physiologically similar to humans and are in abundant supply. Porcine organs are rejected rapidly upon revascularisation, however, by a humoral process called hyperacute rejection (HAR). This is caused by naturally-occurring antibodies in the recipient which recognise and cross-react with antigens on the endothelial cells (ECs) of the xenograft. This recognition triggers the complement cascade which in turn leads to rejection.

European patent 0495852 (Imutran) suggests that membrane-bound regulators of host complement should be expressed on the xenograft in order to prevent the complete activation of complement in the organ recipient. This approach has been developed and applied in order to produce transgenic animals with organs designed to survive hyperacute rejection [eg. refs 1 & 2].

However, organs surviving HAR are subject to delayed xenograft rejection (DXR). This is characterised by the infiltration of recipient inflammatory cells and thrombosis of graft vessels, leading to ischaemia. WO98/42850 shows that expression of coagulation inhibitors on the surface of the xenograft can inhibit the thrombotic aspect of this type of rejection.

HAR and DXR are followed by the host T lymphocyte-mediated response. There are two pathways, "direct" and "indirect" by which T-cells may become sensitised against xenoantigens. The direct pathway involves interactions between T-cells and MHC molecules on xenogeneic donor cells, whereas the indirect pathway involves the presentation of processed xenoantigens by host APCs in the context of MHC class II. The indirect T-cell response is much stronger against xenoantigens than against alloantigens [3], which contrasts with findings for the direct pathway [4], indicating that both the direct and indirect human T-cell responses against xenoantigens must be suppressed if xenotransplantation is to be effective.

It appears that the suppression of anti-xenograft indirect T-cell responses will be one of the greatest challenges for xenotransplantation [5,6]. Maintaining the level of immunosuppression required to prevent chronic xenograft rejection due to persistent indirect immunogenicity may be unfeasible using conventional systemic immunosuppressive drugs because of the increased the risks of infection and neoplasia [eg. 7]. Clearly, if xenotransplantation is to be clinically successful, methods to promote graft-specific immunosuppression are needed in order to reduce the requirements for systemic therapy.

T-cell activation requires two separate signals. Delivery of signal 1 alone induces a refractory state ("anergy"), defined as the inability to produce IL-2 after subsequent antigenic exposure. For full activation to occur, the cell must be co-stimulated with signal 2.

In vivo, signal 1 is provided by the interaction of the TCR/CD4 complex with either allogeneic MHC or antigenic peptide complexed with self MHC; signal 2 is supplied by the interaction between B7 molecules (B7.1 and B7.2, also known as CD80 and CD86, respectively) on the antigen-presenting cell (APC) and CD28 on the T-cell.

Monoclonal antibodies (mAbs) have played a key role in studying T-cell activation. Signal 1 can be supplied by mAbs directed against the TCR/CD3 complex, and mAbs against CD28 can provide signal 2. Indeed, T-cells can be activated by two suitable mAbs, even in the absence of APC. Activation can also be prevented, rather than provided, using mAbs. Signal 2 can be blocked, for instance, using mAbs which block either B7 or CD28.

Signal 2 can also be blocked by using modified forms of CTLA-4, a high-affinity ligand for B7. CTLA-4 is a natural negative regulator of T-cell activation, and B7 binding to CTLA-4 on an activated T-cell antagonises the co-stimulatory signal provided by the B7/CD28 interaction. Soluble forms of CTLA-4, consisting of the extracellular domains of CTLA-4 linked to the constant domain of an antibody, have been constructed [8,9] to block T-cell activation. These molecules ("CTLA4-Ig" or "CTLA4-Fc") behave in a similar way to anti-B7 antibodies and have been used in vitro and in vivo to prevent the co-stimulatory functions of B7 and thus promote tolerance [10].

Targeting the B7/CD28 interaction to prevent T cell sensitisation to graft antigens in vivo has been shown to be an effective strategy to enhance graft survival. Using CTLA4-Ig, prolonged survival has been obtained in various allograft models [eg. 11] and in a human-to-murine islet xenograft model [12]. In the xenograft model, CTLA4-Ig administration caused full tolerance against the xenoantigens by rendering direct-reactive T cells anergic.

It is thus an object of the invention to provide means to promote xenograft-specific immunosuppression. In particular, it is an object of the invention to inhibit T-cell-mediated rejection of xenotransplanted organs by preventing the organ recipient's T-cells from mounting an immune response against the organ. More specifically, it is an object to prevent this immune response by inducing anergy in the recipient's T-cells which recognise the xenotransplanted organ, resulting in xenograft-specific T-cell tolerance.

DESCRIPTION OF THE INVENTION

The invention provides methods and biological reagents for inhibiting T-cell mediated rejection of a xenotransplanted organ by blocking the delivery of co-stimulatory signal 2 in order to prevent the activation of xenoreactive T-cells in the recipient.

This is embodied in three aspects, which are illustrated in FIG. 1. It will be appreciated that these three aspects can be used in isolation or in various combinations. Furthermore, conventional immununosuppressive techniques may be used alongside those of the invention.

The following should be read in conjunction with the section entitled "Definitions", which begins on page 8.

The First Aspect

In a first aspect, co-stimulation by signal 2 is prevented by administration to the organ recipient of a soluble form of CTLA-4 from the xenogeneic donor organism. If, for instance, a pig organ (donor) were being transplanted into a human (recipient), a soluble form of porcine CTLA-4 (see below) would be administered to the human.

Although CTLA-4 from one organism (eg. pig) is able to bind to B7 from another organism (eg. human), the highest avidity is found for allogeneic B7. Whilst soluble CTLA-4 from the donor organism can thus bind to both recipient B7 (on normal cells) and donor B7 (on xenotransplanted cells), it preferentially binds B7 on the xenograft. This results in xenograft-specific immunosuppression, unlike the administration of CTLA-4 from the recipient organism, which would tend to lead to systemic immunosuppression. By blocking the interaction between B7 on the xenogeneic donor cells and CD28 on recipient T-cells, co-stimulatory signal 2 is not delivered to the T-cell of the recipient. Xenoreactive recipient T-cells are therefore rendered anergic.

The invention thus provides a method of inducing xenotransplant tolerance in an organ recipient, comprising the administration to said recipient of a soluble form of the CTLA-4 protein from the xenogeneic donor organism.

The soluble form of CTLA-4 preferably comprises a fragment of the CTLA-4 from the donor organism which retains the ability to bind B7. This fragment is preferably the complete extracellular domain of CTLA-4.

Preferably, the soluble protein further comprises the constant domain of an immunoglobulin (eg. the Cγ1 chain of IgG1). Preferably, this is from the recipient organism, in order to prevent an immune response against this portion of the molecule.

In a typical embodiment for pig-to-human transplantation, therefore, the soluble protein could comprise the extracellular domain of porcine CTLA-4 fused to a human Cγ1 sequence.

Soluble forms of CTLA-4 from other organisms are described in, for instance, references 8 (human CTLA-4/human Ig γ1 constant region) and 9 (murine CTLA-4/human Ig γ1).

The invention also provides the use of a soluble form of xenogeneic CTLA-4 in the preparation of a medicament for inducing xenograft tolerance in an organ recipient.

The protein may be administered before, during, or after the xenotransplantation. Pre-xenotransplantation administration is most useful when the recipient is undergoing a pre-transplantation immunisation programme involving exposure to xenogeneic cells.

In the context of a pig being the donor organism, the invention provides a protein comprising the amino acid sequence shown in FIG. 2 as SEQ ID:1, which is CTLA-4 cloned from porcine cells. This is the preferred form of CTLA-4 for use in the invention. The extracellular domain of this protein is also shown in FIG. 2.

The invention also provides nucleic acid which encodes protein SEQ ID:1 (or fragments thereof). This preferably comprises the nucleotide sequence shown in FIG. 3 as SEQ ID:2.

In addition, the invention provides a vector comprising the nucleic acid of the invention, and a cell transformed with such a vector.

The Second Aspect

In a second aspect, co-stimulation by signal 2 is antagonised by expressing a ligand for CTLA-4 on the xenogeneic donor cells. This ligand binds to CTLA-4 on activated T-cells of the recipient and antagonises the co-stimulatory signal provided by the interaction between donor B7 and recipient CD28. This renders xenoreactive T-cells anergic.

The invention thus provides a membrane-associated protein which can bind to CTLA-4.

This will typically be a chimeric protein (ie. a protein produced by combining regions of different proteins into a single protein) comprising a CTLA-4-binding region and a membrane-association region. In its simplest form, the protein will thus be a fusion protein.

By "membrane-associated protein", it is meant that the protein is attached to a cell membrane such that its extracellular domain can bind to CTLA-4. In order to attach the protein to the cell membrane, the protein might comprise a transmembrane sequence from a membrane protein, for instance, or a GPI anchor. A preferred transmembrane sequence is that of CD4 or CD8. Alternatively the protein might include a sequence which enables it to associate extracellularly with a membrane protein without the protein itself being inserted into the cell membrane.

It may also be desirable for the protein to comprise the cytoplasmic domain which is usually associated with said transmembrane regions (eg. the CD8 cytoplasmic domain), such that the protein is targeted to the cell membrane. Similarly, it may be desirable for the protein to comprise the extracellular sequences immediately juxtaposed with the cell membrane (eg. CD4 domains 3 and 4) in order to separate the CTLA-4-binding domain from the cell membrane. Synthetic linkers, such as glycine linkers, can be used for the same purpose.

The CTLA-4-binding domain of the protein preferably comprises an antibody with specificity for CTLA-4. This is preferably a single chain antibody (sFv). It is preferably specific for the CTLA-4 of a recipient organism.

In a typical embodiment, therefore, a protein of the second aspect can comprise a single chain antibody fused via a linker to the transmembrane and cytoplasmic domains of CD8.

The invention also provides nucleic acid which encodes a protein of the second aspect.

In addition, the invention provides a vector comprising said nucleic acid of the invention, and a cell transformed with said vector.

The invention also provides a delivery system comprising nucleic acid, and/or vector according to the second aspect of the invention, and means to deliver this material to a target cell.

Furthermore, the invention provides a cell which expresses a protein of the second aspect on its surface, preferably such that the protein can bind to available CTLA-4.

So that the cell can engage recipient T-cells, the cell preferably also expresses MHC (class I or class II) on its surface. Suitably, therefore, the cell of the invention is a donor professional APC. Because of the antagonistic signal provided by the anti-CTLA-4 protein, however, these professional APC behave functionally as B7-negative cells.

The invention also provides biological tissue comprising such a cell.

The invention further provides an animal comprising a cell and/or biological tissue according to the second aspect.

The invention also provides a process for rendering biological tissue suitable for xenotransplantation, comprising the step of treating said biological tissue such that it expresses one or more proteins according to the second aspect on the surface of its cells.

The invention also provides a method of transplantation comprising the step of transplanting biological tissue according to the invention from a donor animal (eg. a pig) into a xenogeneic recipient animal (eg. a human).

In addition, the cells of the invention are suitable for pre-transplantation administration. This results in tolerance being induced in recipient T-cells before the xenograft itself is transplanted. Whilst the cells used in such pre-transplantation regimes should preferably express MHC class II, it will be appreciated that the cells need not be professional APCs.

Furthermore, the invention provides protein or nucleic acid according to the second aspect for use as a medicament.

The invention also provides the use of protein, nucleic acid, a vector, or a delivery system according to the second aspect in the manufacture of a formulation for administration to a xenotransplant recipient or donor.

The Third Aspect

In a third aspect, co-stimulation by signal 2 is prevented by expressing recipient organism MHC class II on the surface of the cells of the xenogeneic donor organ. If, for instance, a pig organ (donor) were being transplanted into a human (recipient), the pig organ would express human MHC class II.

Even if direct activation of recipient T-cells is avoided, for instance by utilising one or both of the first two aspects of the invention described above, indirect activation can still occur, involving the processing and presentation of xenoantigens on MHC class II by recipient APC.

By expressing recipient MHC class II on the cells of the xenogeneic donor, the donor cells will present xenoantigens to a recipient T-cell in the context of self MHC class II. If the donor cells do not express B7, or if B7 is blocked, the xenoreactive recipient T-cell will not receive co-stimulatory signal 2 and will become anergic before the recipient's APCs have an opportunity to present the xenoantigens themselves.

The invention thus provides a cell which expresses on its surface MHC class II of a different organism. Preferably, this is a porcine cell expressing human MHC class II on its surface.

The MHC class II is preferably of the HLA-DR family.

The MHC class II is preferably constitutively expressed on the surface of the cells.

In order to prevent an allogeneic anti-MHC class II response, the MHC class II is preferably tissue-typed for maximum compatibility with the particular recipient. This will typically involve, for instance, ensuring that the HLA-DR expressed on the xenogeneic donor cell should match the HLA-DR of the particular recipient.

To ensure that xenoantigen display within the groove of the MHC class II molecule mirrors that found on professional APC, it is preferred that the cell should also express one or more of the following three proteins, each of which has an important role in antigen processing: invariant chain, HLA-DMα and HLA-DMβ.

The cell preferably does not express co-stimulatory molecules (eg. B7) on its surface. Typically, therefore, the donor cell is not a professional APC. It may, however, be a transfected non-immunogenic APC, such as an immature dendritic cell, which may be B7$^+$.

The invention also provides biological tissue comprising a cell according to the third aspect.

The invention further provides an animal comprising a cell and/or biological tissue according to the third aspect.

The invention also provides a process for rendering biological tissue suitable for xenotransplantation, comprising the step of treating said biological tissue such that it expresses xenogeneic MHC class II on the surface of its cells.

Preferably, this process comprises the steps of isolating non-immunogenic cells (ie. cells which cannot provide a co-stimulatory signal, such as B7-negative cells) from a xenogeneic organism and transfecting these cells with HLA-DR. The HLA-DR is preferably tissue-typed for a specific recipient. Furthermore, the cells may also be transfected with other proteins necessary for efficient antigen processing. Examples of suitable non-immunogenic cells include renal tubular epithelial cells, which are B7-negative and have been shown to induce tolerance in rodent models of allogeneic transplantation.

The invention also provides a method of transplantation comprising the step of transplanting biological tissue according to the third aspect from a donor animal (eg. a pig) into a xenogeneic recipient animal (eg. a human).

In addition, the cells of the invention are suitable for pre-transplantation administration. This results in tolerance being induced in recipient T-cells before the xenograft itself is transplanted.

Furthermore, the invention provides a cell according to the third aspect for use as a medicament.

The invention also provides the use of a cell or of biological tissue according to the third aspect in the manufacture of a formulation for administering to a xenotransplant recipient.

The invention also provides the use of xenogeneic MHC class II, or nucleic acid encoding xenogeneic MHC class II, in the preparation of a formulation for administering to a xenotransplant donor.

DEFINITIONS

As used above, the term "nucleic acid" includes both DNA and RNA, although modified and synthetic nucleic acids are also included, For instance, the nucleic acid may be synthetic (eg. PNA), or may have modified inter-nucleotide linkages (eg. phosphorothioates). Furthermore, the term includes both sense and antisense nucleic acid sequences, as well as double-stranded sequences.

Preferably the nucleic acid comprises sequences suitable for the regulation of expression of protein according to the invention. This expression can preferably be controlled, such as cell-specific control, inducible control, or temporal control.

As used above, the term "vector" signifies a molecule which is capable of transferring nucleic acid to a host cell, and numerous suitable vectors are known in the art.

Preferably the vector is suitable for the production of a transgenic animal. Vectors suitable for the generation of transgenic pigs, for example, are described in references 13, 14, 15, 16 & 17.

As used above, the term "delivery system" refers to means for delivering genetic material to a target cell.

Certain vectors as described above may also function as suitable delivery systems. Likewise, certain delivery systems may also inherently be vectors, but this is not always the case. For instance, a viral vector can also function as a delivery system, whereas a liposomal delivery system is not a vector. The delivery system may be viral or non-viral. Non-viral systems, such as liposomes, avoid some of the difficulties associated with virus-based systems, such as the expense of scaled production, poor persistence of expression, and concerns about safety. Preferably the delivery system is suitable for use in gene therapy. Numerous appropriate delivery systems are known in the art.

Preferably, the delivery system will be targeted so that molecules according to the invention are taken up by cells suitable for xenotransplantation, or cells which have been transplanted. More preferably the delivery system will be specific for these cells. For example, the delivery system may be targeted to a specific organ, such as the heart or the kidney, or to a specific cell type, such as endothelial cells or professional APC.

To achieve this the delivery system may, for example, be a receptor-mediated delivery system, being targeted to receptors found on target cells. For example, the delivery system may be targeted to receptors found on heart cells, preferably to receptors found exclusively on heart cells, or it may be targeted to receptors found on endothelial cells, preferably to receptors found exclusively on endothelial cells.

The delivery system is preferably suitable for the generation of a transgenic animal. For example, the delivery system may be targeted to a gamete, a zygote, or an embryonic stem cell.

The vectors and delivery systems of the invention can be used to transfect cells to produce cells according to the invention. The transfection can occur in vivo or ex vivo.

The term "biological tissue" as used above includes collections of cells, tissues, and organs. Accordingly the definition includes, for example, fibroblasts, a cornea, nervous tissue, a heart, a liver, or a kidney.

Where the second and third aspects of the invention provide "an animal", said animal is preferably suitable for the production of organs for xenotransplantation and/or cells of the invention (eg. cells for pre-xenotransplant administration to xenograft recipients). Preferably the animal is a mammal, and more preferably it is a transgenic pig or a transgenic sheep.

The animal might be treated whilst alive such that it comprises transgenic biological tissue (ie. treated by gene therapy). Preferably, a live animal is transfected with a vector according to the invention in order to produce a transgenic animal. For example, a vector according to the invention could be specifically delivered to the heart of a pig to produce biological tissue suitable for xenotransplantation.

Alternatively, the animal might be born as a transgenic animal. Many suitable approaches for generating such transgenic animals are known in the art [eg. refs. 18, 19, 20]. For example, direct manipulation of the zygote or early embryo, by microinjection of DNA for instance, is well known, as is the in vitro manipulation of pluripotent cells such as embryonic stem cells. Retroviral infection of early embryos has proved successful in a range of species, and adenoviral infection of zona-free eggs has been reported. Transgenesis and cloning of sheep by nuclear transfer has also been described (eg. WO97/07668).

Where the invention provides a process for rendering biological tissue suitable for xenotransplantation, said biological tissue may be so rendered either in vivo or ex vivo. For example, an animal organ may be in vivo transfected with a vector according to the invention, or an organ could be transfected ex vivo before transplantation or in vivo after transplantation.

BRIEF DESCRIPTION OF THE DRAWINGS

The invention will now be described with reference to the attached drawings, in which:

FIG. 2 shows the amino acid sequence of pCTLA-4 (SEQ ID NO:1). The following junctions are illustrated by a "*": signal peptide/extracellular domain; extracellular domain/transmembrane domain; transmembrane domain/cytoplasmic domain. An alignment with the human and bovine sequences is also shown. Homologies with pCTLA4 are:

| Domain | Human | Bovine |
|---|---|---|
| Signal peptide | 67.6% | 86.5% |
| Extracellular domain | 83.8% | 84.6% |
| Transmembrane domain | 96.1% | 100% |
| Cytoplasmic domain | 100% | 100% |
| Overall | 85.2% | 89.2% |

FIG. 3 shows a similar alignment, but at the nucleotide level. Homologies are as follows:

| Domain | Human | Bovine |
|---|---|---|
| Signal peptide | 76% | 81.3% |
| Extracellular domain | 85.2% | 86.3% |
| Transmembrane domain | 92.3% | 96.2% |
| Cytoplasmic domain | 96.5% | 97.7% |
| Overall | 86.1% | 88.3% |

FIG. 4 shows the amino acid sequence of the pCTLA4-Ig construct. The underlined sequence shows the flexible linker GGSGGAA, which also denotes the junction between pCTLA4 and the IgG1 domains.

Figure 1:
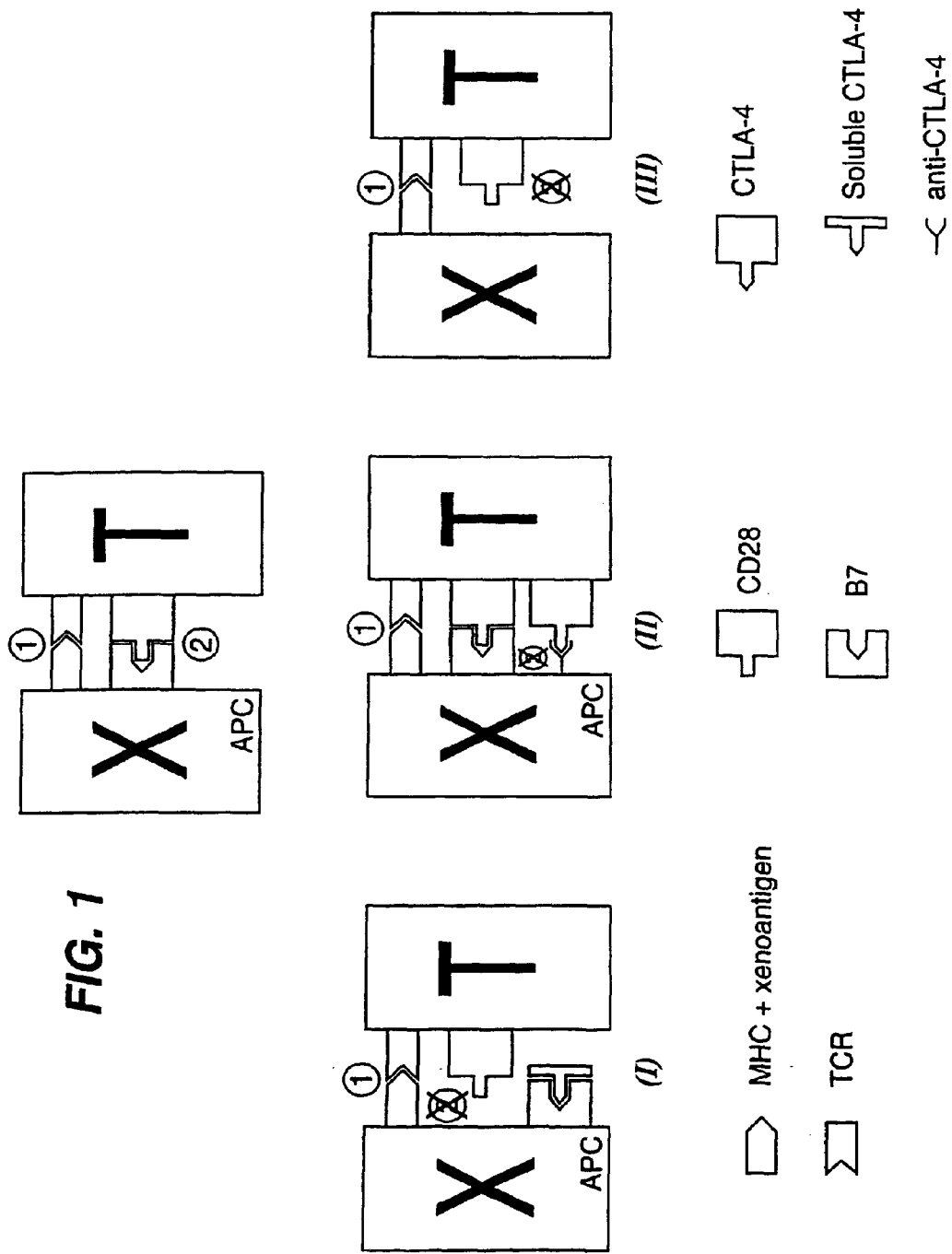
FIG. 1 illustrates the three aspects of the invention. "X" represents a xenogeneic cell (or, in the indirect activation pathway, a xenoantigen-presenting recipient APC), and "T" represents a recipient T-cell. In embodiment I, the delivery of co-stimulatory signal 2 is prevented by using a soluble form of CTLA-4. In embodiment II, anti-CTLA-4 is used to antagonise signal 2. In embodiment III, X expresses recipient MHC-II, but does not express B7.
Figure 5:
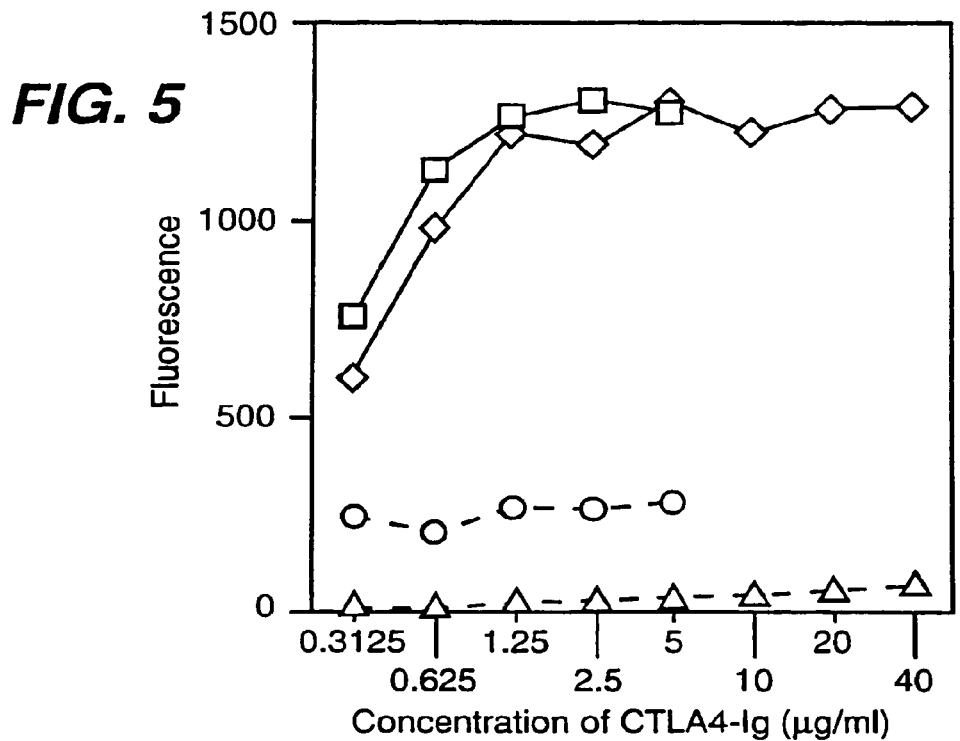

FIG. 5 shows the results of flow cytometric analysis of hCTLA4-Ig (○ &) and pCTLA4-Ig (◇ & △) binding to human fibroblasts transfected with either human B7 (lower two lines) or porcine B7 (upper two lines).

Figure 6:
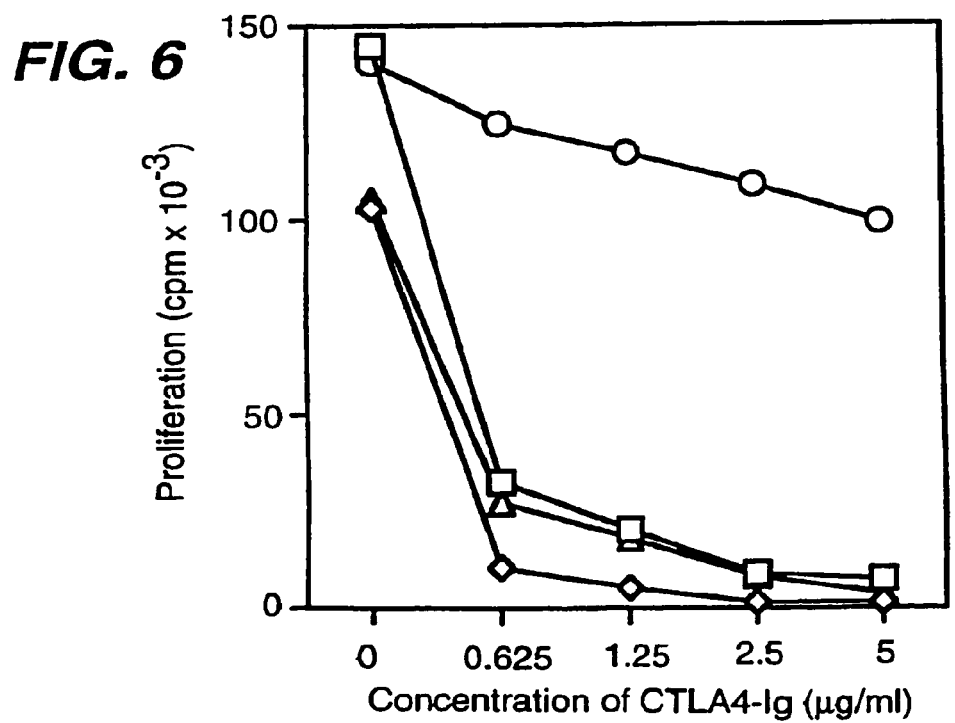

FIG. 6 shows the selective inhibition of proliferation by pCTLA4-Ig (○ & △) compared to hCTLA4-Ig (& ◇) when co-stimulated by human B7 (& ○) or porcine B7 (◇ & △).

Figure 7A:
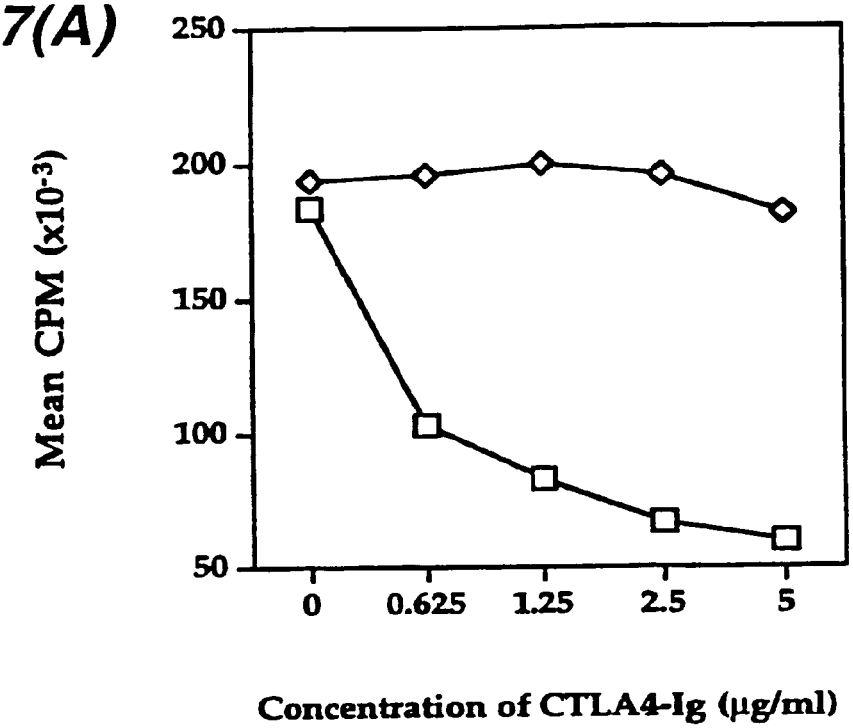
Figure 7B:
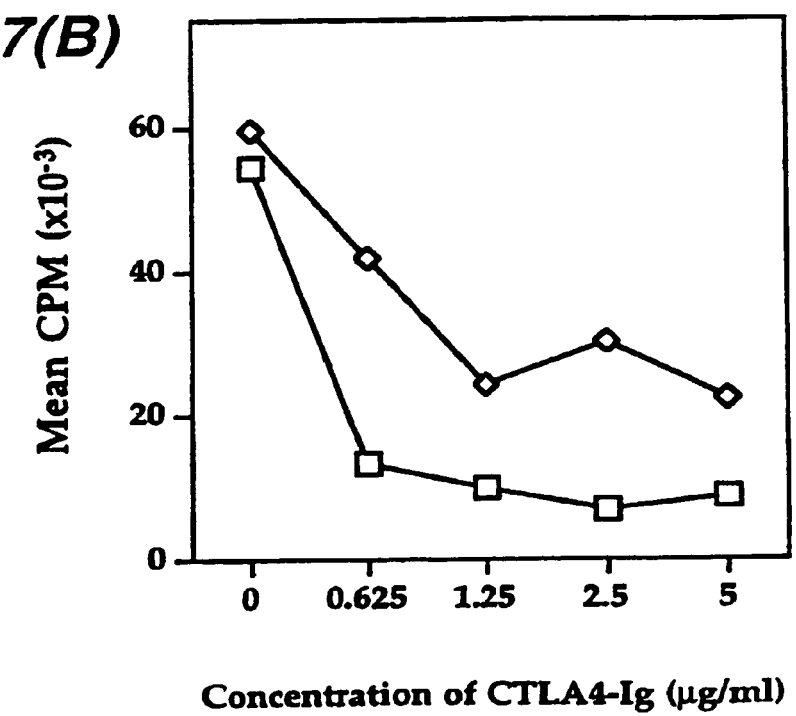

FIG. 7 shows the inhibition of human CD4$^+$ T cell proliferation by hCTLA4-Ig ( ) or pCTLA4-Ig (◇) when human (7A) or porcine (7B) cells expressing MHC-class II were used as stimulators in a five day mixed leukocyte reaction.

FIG. 8 shows the nucleotide sequence of an anti-human CTLA-4 sFv. The inferred protein sequence is shown in FIG. 9.

FIG. 10 shows the nucleotide sequences of four anti-murine CTLA-4 sFv. The inferred protein sequences are shown in FIG. 11. The heavy and light chains are linked by a serine-glycine linker as indicated in FIGS. 9 and 11.

FIG. 12 shows the construct encoding the soluble Ig-fusion of the CTLA-4-specific sFv.

Figures 9, 13:
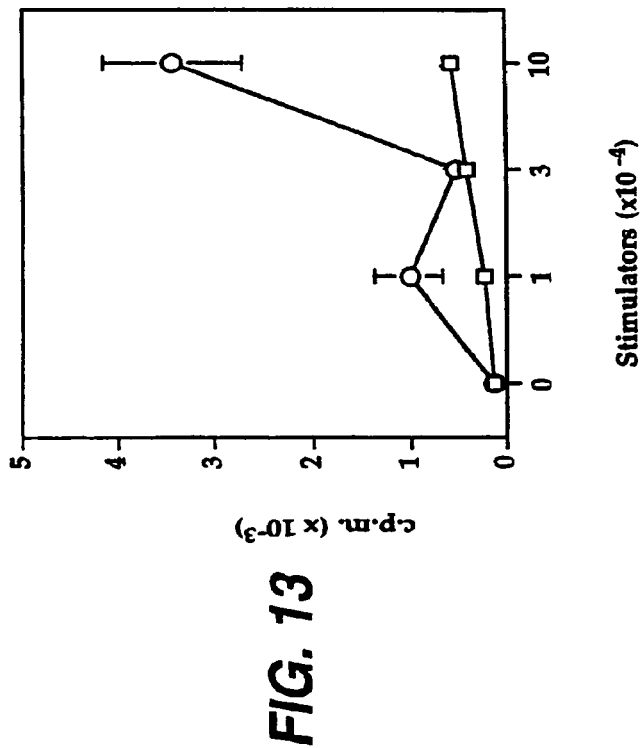

FIG. 13 shows the inhibition of T cell proliferation by cells expressing either an anti-hCTLA-4 sFv ( ) or a control sFv (○).

FIG. 14 shows construct encoding the membrane-bound form of the anti-CTLA-4 sFv.

FIG. 15 shows (A) the nucleotide sequence and (B) the amino acid sequence of human CTLA-4. The start codon is underlined. At position −21, the sequence differs from GenBank sequence L15006, and at position 110 the sequence differs from both L15006 and M74363.

FIG. 16 shows the sequence of cloned human CD8α. This differs from the GenBank sequence at positions 231 (T→G), 244 (A→G), 266 (T→C), and 437 (T→C).

Figure 17:
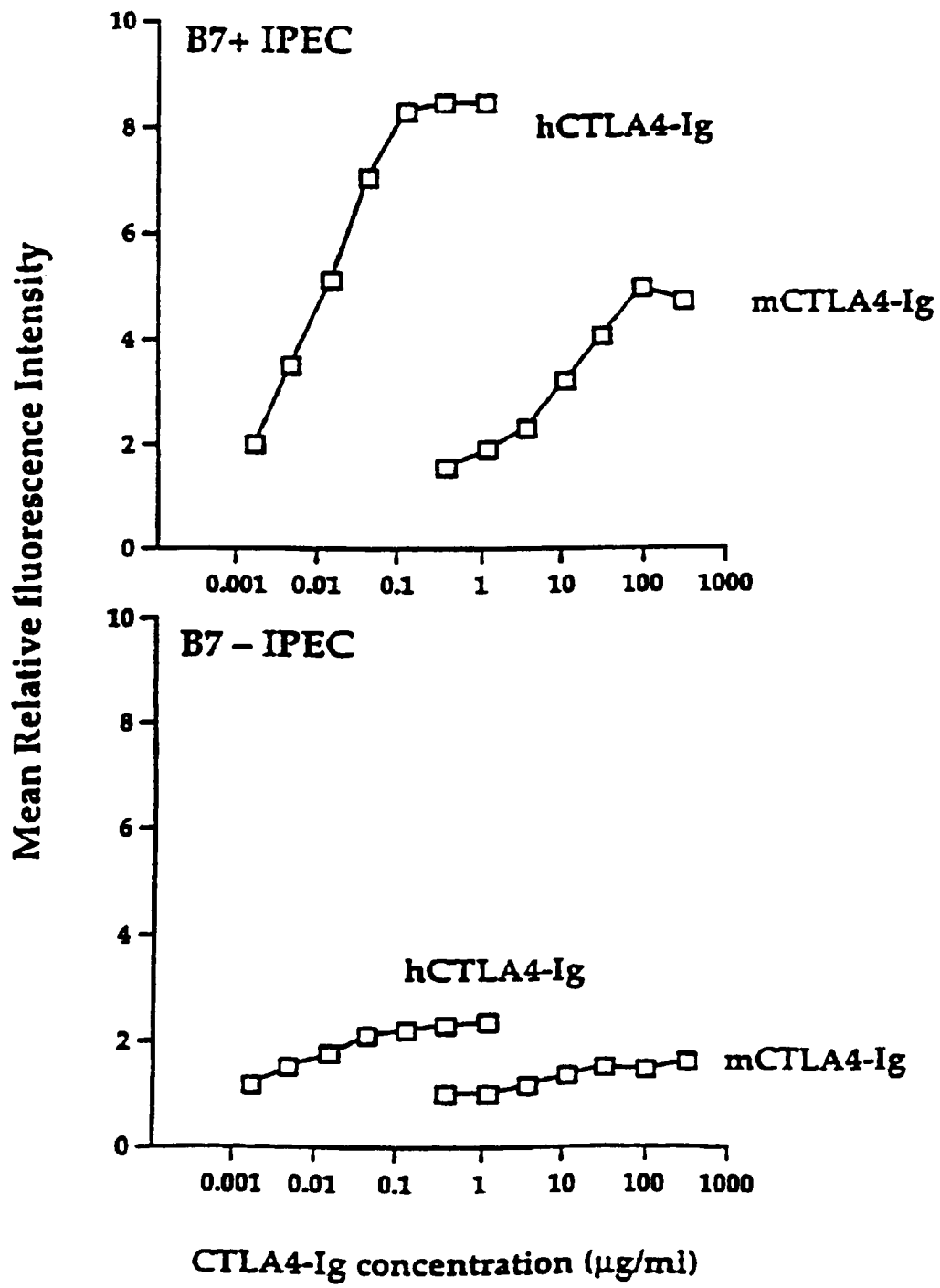

FIG. 17 shows the binding of human and murine CTLA4-Ig to IPEC, in order to define clones as B7-negative or B7-positive.

Figure 18:
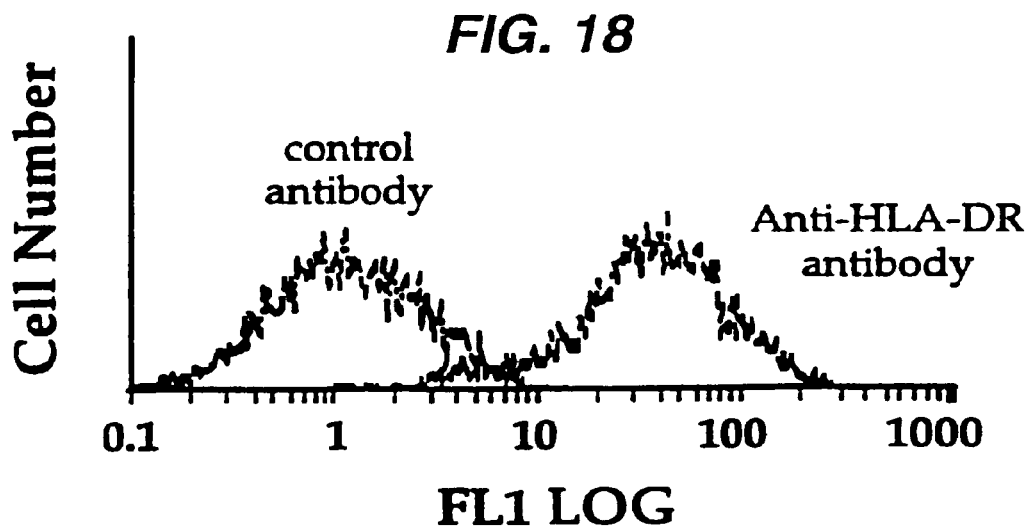

FIG. 18 shows the binding to transfected cells of HLA-DR-specific mAb L243.

Figure 19:
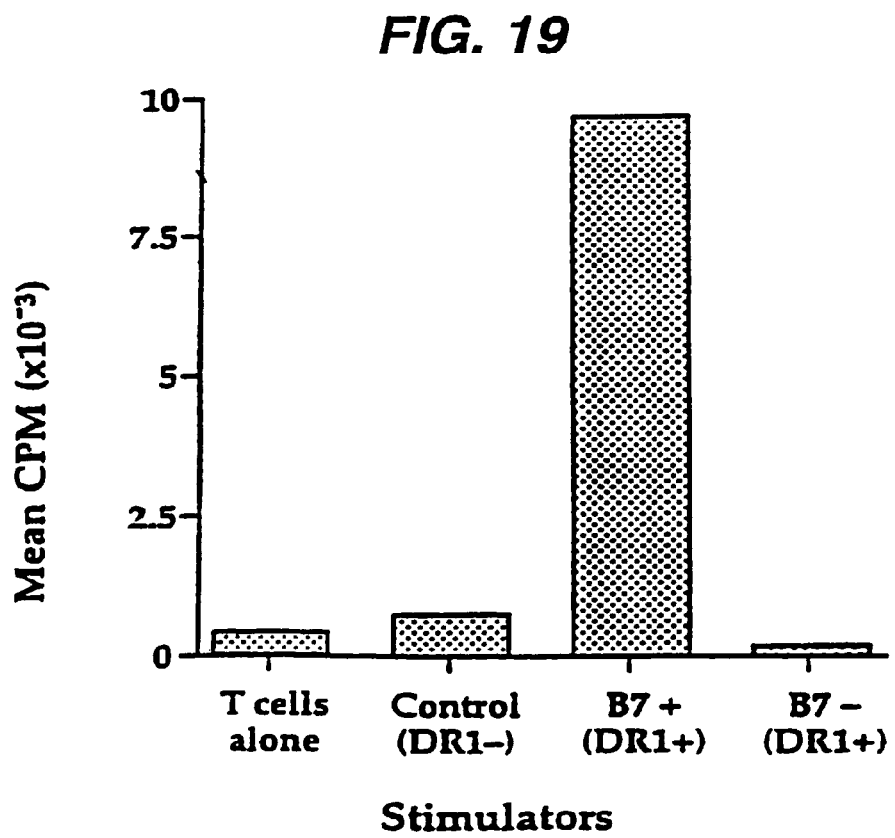

FIG. 19 shows the proliferation by human T-cells to HLA-DR-1 transfected IPEC.

Figure 20:
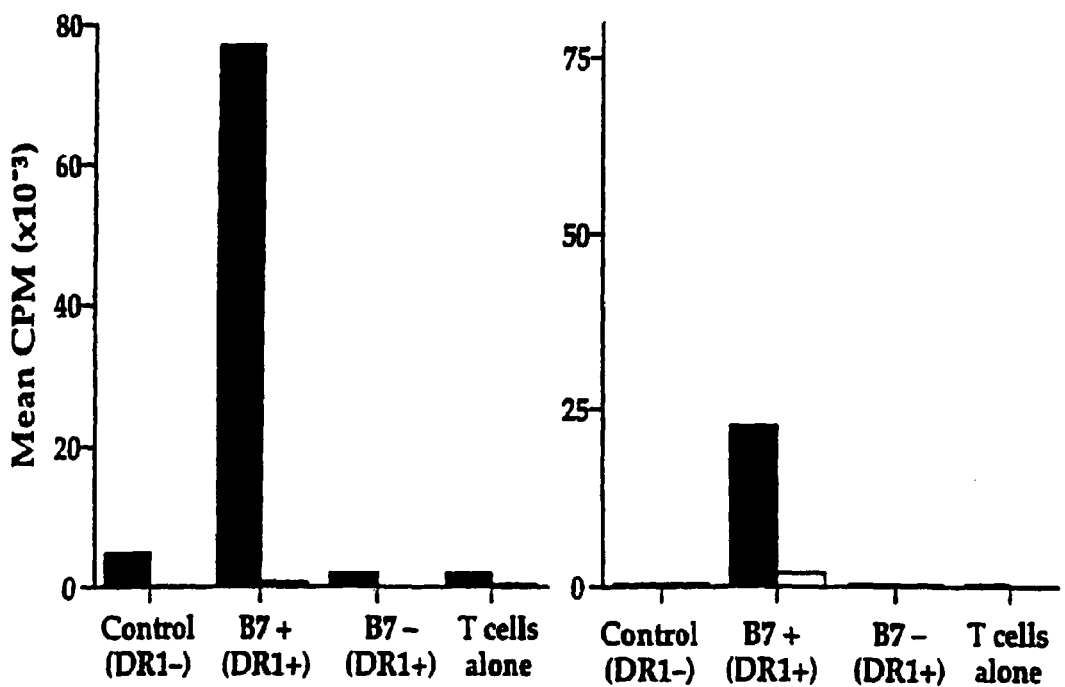

FIG. 20 shows the results of a human T-cell proliferation assay following 2 days of incubation HLA-DR-1 transfected cells. The X-axis indicates the stimulator cells used in the second step of the proliferation assay. The black bars show results with CD4 T-cells which were primed with B7-positive transfectants; the white bars (hardly visible) show results after priming with B7-negative transfectants. The first graph shows results with cells harvested on day 3; the second graph shows results from a harvest on the sixth day.

Figure 21:
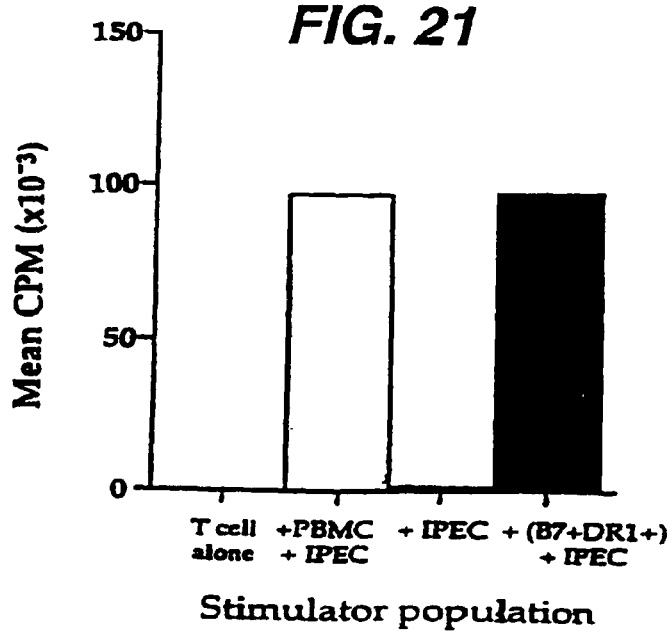

FIG. 21 shows the proliferation of an APC-dependent, HLA-DR-1 restricted T-cell line raised against IPEC. The stimulator population is indicated on the X-axis.

DESCRIPTION OF EMBODIMENTS

Soluble Porcine CTLA-4

Porcine CTLA-4 ("pCTLA4") was cloned from PHA-activated pig T cells. RNA was prepared using standard techniques and pCTLA4 was amplified by PCR using primers:

```
(5' primer)
5'-TTGAAGCTTAGCCATGGCTTGCTCTGGA-3'

(3' primer)
5'-TAATGAATTCTCAATTGATGGGAATAAAATAAG-3'
```

The resulting 700 bp fragment was sub-cloned into EcoRI/HindIII digested pBluescript, and the nucleotide sequence was determined using the standard T3 and T7 primers. The sequence of a single clone is shown in FIG. 3, which also shows a comparison with the human and bovine CTLA-4 sequences.

The predicted amino acid sequence of pCTLA4 is shown in FIG. 2, with a comparison with that of human and cattle. Of significance is the predicted amino acid difference at residue 97, which is important in B7 binding, being part of the conserved hexapeptide motif MYPPPY. In pCTLA4, residue 97 is leucine (giving LYPPPY), whereas other species have methionine (although leucine has also been found in bovine CD28 [21]). This important amino acid difference is believed to be of key importance to the advantageous differential binding of pCTLA4 to human and pig B7.

The extracellular domain of pCTLA4 was amplified using the 5' primer described above and

```
5'-CGGTTCTGCAGCACCACCGGAGCCACCATCAGAATCTGGGCATGG

TTCTGGATCAATGAC-3'
```

This amplified from position 484, introduced an 18 base-pair segment encoding a linker GGSGGAA sequence (underlined), and introduced a PstI site (bold) to allow in-frame ligation to the hinge region of human IgG1. The resulting 500 bp fragment was sub-cloned into HindIII/PstI digested pBluescript-IgG1 containing genomic DNA encoding intronic sequences and the hinge, CH2, CH3 and 3' untranslated exons of human IgG1 between PstI/NotI sites. The amino acid sequence of the resulting soluble pCTLA4-Ig is shown in FIG. 4.

Expression of pCTLA4-Ig

The chimeric pCTLA4-Ig DNA sequence was released from pBluescript as a HindIII/BstXI fragment and was sub-cloned into the expression vector pHOOK-3™ (Invitrogen). This was used to transfect DAP.3 or CHO-KI cells using standard calcium phosphate precipitation. G418-resistant cells were separated using the CaptureTec™ system. These transfected cells were grown in tissue culture flasks until confluent, at which point the medium was changed, and the cells were kept in culture for a further 3 days. At this stage the medium was harvested and perfused through a protein G column. pCTLA-4-Ig was eluted under acid conditions. The concentration of the eluted protein was calculated using ELISA with an antibody directed against human IgG1 and a standard human IgG1 myeloma protein.

The binding characteristics of pCTLA4-Ig were compared to those of human CTLA4-Ig using flow cytometric analysis with human fibroblasts transfected with either human B7-1 or porcine B7-2. For these experiments, the concentration of pig and human CTLA4-Ig were equivalent as assessed by ELISA. As illustrated in FIG. 5, human and porcine CTLA4-Ig appeared to have similar binding characteristics on human cells expressing porcine B7. Unlike human CTLA4-Ig, however, pCTLA4-Ig failed to bind human B7, implying that pCTLA4-Ig binds preferentially to porcine B7 and is useful as a species-specific reagent.

pCTLA4-Ig was used to inhibit human T cell proliferative responses to a variety of stimulators. In these assays, co-stimulation of the T cell response was provided by either porcine or human B7, expressed either by transfection or naturally on professional APCs. These experiments are demonstrated in FIGS. 6 and 7.

In the experiments using transfected fibroblast stimulators (expressing HLA class II and either human or pig B7), hCTLA-Ig inhibited all proliferative responses (FIG. 6, & ◇). In contrast, pCTLA4-Ig only fully inhibited the response when stimulators expressed porcine B7 (Δ); the proliferative response to cells expressing human B7 was only minimally affected (○).

In similar experiments, pCTLA4-Ig failed to have a significant inhibitory effect on the proliferative responses to human cells expressing MHC class II and human B7 but did inhibit the response to porcine stimulators (FIG. 7).

These results highlight the effective inhibitory properties of pCTLA4-Ig when T cell co-stimulatory signals are provided by porcine B7. The failure to prevent T cell proliferation when co-stimulation is mediated by human B7 also demonstrates species-specific action. It can be concluded that pCTAL4-Ig shows species-specific binding to and inhibition of the functional effects of porcine B7, but not human B7.

Properties of pCTLA-4-Ig

The binding characteristics of pCTLA4-Ig to both human and porcine B7-family molecules may be compared to those of hCTLA4-Ig, for example using the following tests:
  (i) flow cytometric analysis of binding to porcine and human APC, and to transfectants expressing porcine or human B7 (see above)
  (ii) quantitative characterisation of binding using Biacore™.
  (iii) functional analysis of the effects of CTLA4-Ig on human anti-pig and human allogeneic mixed lymphocyte cultures.
  (iv) functional assessment of the ability of pCTLA4-Ig to prolong porcine islet xenograft survival after transplantation into B6 mice.

A Membrane-Associated Protein which Binds to CTLA-4

A phage display library containing $10^{12}$ semi-synthetic variable sequences was screened using human or murine CTLA4-Ig and a control human IgG1 myeloma protein. The sFv from a phage displaying differential binding to the human CTLA4-Ig protein after 4 rounds of screening were isolated and purified using standard techniques. The nucleotide and inferred amino acid sequences are shown in FIGS. 8, 9, 10, and 11.

The sFv were amplified by PCR using specific primers based on the nucleotide sequences. The distal portions of the primers were based on sequence within pHOOK1. The 5' primer contained an ApaI site and the 3' primer contained a SalI site, both of which were predicted to be unique. The resulting sFv were sub-cloned into pBluescript for sequencing to determine faithful amplification. The ApaI/SalI fragments were then sub-cloned into pHOOK1, where it is flanked upstream by an in-frame signal sequence from the murine Ig κ-chain and a haemaggluttinin A epitope sequence, and downstream by two in-frame myc sequences and a transmembrane sequence from the PDGF receptor.

The myc sequences from pHOOK1 were amplified by PCR using the 5' primer 5'-GAGCTGAAACGG GCGGCCGCAGAAC-3', which contains a NotI site (underlined) and the 3' primer 5'-CTGGC CTGCAGCATTCAGATCC-3', which introduced a PstI site (underlined). The resulting 113 base pair fragment was sub-cloned into NotI/PstI digested pBluescript.

The sFv was released from pHOOK1 as an EcoRI/NotI fragment, and was ligated into EcoRI/PstI digested pBluescript-IgG1, along with the NotI/PstI PCR product [FIG. 12]. This construct encodes a soluble Ig-fusion of the CTLA-4-specific sFv. For expression in eukaryotic cells, the construct was sub-cloned into pHOOK3 as a HindIII/BstXI fragment.

To confirm cell-surface expression of the sFv, the pHOOK construct was transfected into cells already expressing HLA-DR molecules and human B7. Cells resistant to G418 or mycophenolic acid, depending on the vector used, were grown in culture. Cells expressing the anti-CTLA4-sFv construct on the cell surface were identified by flow cytometric analysis using hCTLA4-Ig. These cells were cloned by limiting dilution and were used as stimulators of T cell proliferation in 5 day cultures. The results of one experiment are shown in FIG. 13. Cells expressing the anti-hCTLA4 sFv failed to stimulate T cell proliferation ( ), whereas those expressing a control sFv stimulated proliferation in the same way as normal cells (○).

In different experiments, the EcoRI/SalI fragment of the construct shown in FIG. 12 was co-ligated with the transmembrane and cytoplasmic domains of human CD8 (isolated as a SalI/BamHI fragment from pBluescript-hCD8) into EcoRI/BamHI digested pBluescript [FIG. 14].

The EcoRI/BamHI fragment from pBluescript was sub-cloned into the expression vector pHβApr-1-neo or the sister vector pHβApr-1-gpt. These were transfected into cells already expressing HLA-DR molecules and B7 and selected as described above for the pHOOK construct.

Membrane-Associated CTLA-4 Construct

The expression of CTLA-4 on by activated T-cells is only transient so, to test the functional characteristics of the anti-CTLA4-sFv, chimeric constructs comprising the DNA sequences encoding the extracellular domains of human or murine CTLA4 and the transmembrane/cytoplasmic sequences of human CD8 were made. Cells expressing these constructs can be used for the study of the anti-CTLA4-sFv protein.

RNA from PHA-activated human T cells was prepared using standard techniques. hCTLA4 was amplified PCR using primers:

```
introducing a Hind-III site (5' primer)
5'-TTCAAAGCTTCAGGATCCTGAAAGGTTTTG-3' introducing an EcoRI site (3' primer)
5'-TAATGAATTCTCAATTGATGGGAATAAAATAAG-3'
```

The resulting fragment was sub cloned into HindIII/EcoRI digested pBluescript and the nucleotide sequence: determined using standard T3 and T7 primers. The sequence of a single clone is shown in FIG. 15. This differed by a single base (position 439) from GenBank-listed sequences for human CTLA-4. The predicted amino acid sequence of hCTLA4 is also shown.

The extracellular domain of hCTLA-4 was amplified using 5' primer described above and:

```
5'-GATGTAGATATCACAGGCGAAGTCGACACCACCGGAGCCACCAAT

TACATAAATCTGGGCTCCGTTGCCTATGCCC-3'
```

This amplified from position 457 and included a 15 base segment encoding a flexible GGSGG amino acid linker (underlined), along with a unique SalI site (highlighted). The resulting fragment was sub cloned into HindIII/SalI digested pBluescript and sequenced.

hCD8 was PCR-amplified from resting T-cells using primers:

```
introducing a HindIII site (5' primer)
5'-TCGCGCCCAAGCTTCGAGCCAAGCAGCGT-3 introducing an EcoRI site (3' primer)
5'-TAATGAATTCTCAATTGATGGGAATAAAATAAG-3
```

The resulting fragment was sub cloned into HindIII/EcoRI digested pBluescript and the nucleotide sequence determined using standard T3 and T7 primers. The sequence of a single clone is shown in FIG. 16. This clone differed from the sequence deposited with GenBank at four positions, although none of these were within the region that was subsequently amplified.

The transmembrane (TM) and cytoplasmic (C) domains of hCD8 were amplified using the 3' primer described above and the following 5' primer:

```
5'-CATAGGCAACGGAGCCCAGATTTATGTAATTGGTGGCTCCGGTGG

TGTCGACTTCGCCTGTGATATCTACATC-3'
```

This amplified from position 532 and included a 15 base segment encoding a flexible GGSGG amino acid linker (underlined), along with a unique SalI site (highlighted). The resulting fragment was sub cloned into HindIII/SalI digested pBluescript and called pBluescript-hCD8.

The extracellular domain of human CTLA-4 was cut from pBluescript as an EcoRI/SalI fragment, and the TM-IC domain of CD8 cut as a SalI/BamHI fragment. Together they were ligated back into EcoRI/BamHI digested pBluescript. The whole CTLA-4-CD8 chimera was then removed as a single EcoRI fragment and was sub-cloned into a number of expression vectors for expression into the human T cell leukaemia line J6.

Properties of the Cell-Surface Anti-CTLA4 Proteins

The cell-surface anti-CTLA-4 proteins may be further characterised by the following functional tests:

i) Flow cytometric assessment of the interaction between cells expressing the membrane-bound anti-CTLA4-sFv-CD8 protein and soluble human CTLA4-Ig.
ii) Quantitative assessment of the interaction between the soluble anti-CTLA4-sFv-Ig fusion protein and soluble human CTLA4-Ig, using Biacore™
iii) Analysis on the signalling events resulting from the binding of soluble human CTLA4-Ig to J6 transfectants expressing the anti-CTLA4-sFv-CD8 fusion protein.

iv) Analysis of T cell responses (eg. proliferation, cytokine production, anergy induction) when stimulation in an allogeneic mixed lymphocyte response is provided by an HLA-DR-positive, B7-positive, anti-CTLA4-sFv-CD8-positive cell line.

B7-Negative Porcine Cells Expressing Murine MHC Class II

Fifty cloned immortalised porcine aortic endothelial cells (PAEC) were generated from monolayers of PAEC by intranuclear microinjection with pZipSVU19 DNA [22]. From the immortalised cells (IPEC), B7-negative clones were identified by flow cytometric screening with hCTLA4-Ig and mCTLA4-Ig [see FIG. 17]. These were then transfected with cDNAs encoding HLA-DRA and DRB1*0101 in the plasmid expression vectors pcExV1-gpt and pHβApr-1neo, and cells were placed under selection with MXH and G418. For comparison, B7-positive IPEC controls were generated similarly [4].

Another series of IPEC transfectants expressing the murine MHC class II molecule I-A$^b$ were also generated for experiments in mice.

Surface expression of MHC class II on transfected IPEC cells was detected using monoclonal antibody L243 (specific for HLA-DR) [FIG. 18] or M5-114 (specific for murine MHC class II). MHC class II-positive cells underwent several rounds of fluorescence activated cell sorting before being cloned by limiting dilution.

A second batch of transfectants was prepared in exactly the same way, but with additional transfected cDNAs encoding HLA-DMA and HLA-DMB and p31Ii (invariant chain) in the expression vector pCMU.

Anergy Induction in Allogeneic T-Cells by MHC Class II-Expressing Cells

Human T-cells were purified using standard protocols [3]. For primary proliferation assays, T-cells were incubated for 5 days with fixed numbers of irradiated stimulator cells, before addition of 1 µCi $^3$H-thymidine sixteen hours prior to harvesting onto glass fibre filters. The filters were read in a scintillation counter.

B7-positive IPEC caused significant, anti-DR1 specific proliferative responses, whereas B7-negative IPEC failed to initiate any proliferative response [FIG. 19].

Two step anergy induction assays were established by a standard protocol [23]. In the primary, tolerance-induction step, T-cells incubated with B7-positive IPEC mounted an anti-DR1 proliferative response in the secondary step with the kinetics of a primed secondary immune response (maximal at three days). However, T-cells incubated with B7-negative IPEC in the primary step became tolerant to DR1 and failed to mount a response on subsequent exposure to DR1-expressed on B7-positive IPEC [FIG. 20].

Anergy Induction in DR1-Restricted T Cells by DR1-Expressing Pig Cells.

CD4$^+$ T-cells from a DR1-expressing individual were purified according to standard procedures. In primary proliferation assays, they proliferated to B7-positive IPEC transfected with HLA-DR1, indicating that the DR1 can perform as a restriction element for pig-peptide-specific T-cells. Assays comparing the proliferative response to B7-positive and B7-negative DR1+ transfectants are being performed.

Two step anergy induction assays may also be performed to demonstrate that DR1-transfected, B7-negative pig cells induce anergy in HLA-DR-restricted human T-cells.

Overlap Between the Pig Peptides Processed by Professional Human APC for Presentation on HLA-DR and Those Presented on MHC Class II of IPEC Transfected with HLA-DR.

A human T-cell line against wild type IPEC was raised from human PBMC. The proliferative response of this line was dependent on the presence of human APC and inhibitable by antibodies against HLA-DR, indicating that the line had indirect specificity for processed porcine xenoantigens presented by human APC.

This line proliferated against B7-positive HLA-DR1-transfected IPEC [FIG. 21] implying that at least some of the processed pig peptides presented indirectly by professional human APC are also presented by transfected pig cells.

Studies in Pig-Islets-to-Mouse Model

In vivo, porcine pancreatic islet cells may be transplanted under the kidney capsule of streptozotocin-treated diabetic mice. Islet xenografts, being non vascular, are rejected solely by T-cells. Porcine islets are prepared from the pancreas of pigs under terminal anaesthesia, and their survival in the recipients assessed by maintenance of normoglycaemia. Mice are injected intravenously with B7-negative, I-A$^b$-expressing IPEC before transplantation of pig islets. This strategy can be combined with other aspects of the invention to tolerise the direct pathway of T-cell recognition, to ensure that rejection via the direct pathway does not occur. To assess whether a particular strategy has induced specific T-cell tolerance, nephrectomy of the islet-carrying kidney is performed before re-transplantation (under the capsule of the surviving kidney), of identical or third party porcine islets.

It will be understood that the invention is described above by way of example only and modifications may be made whilst remaining within the scope and spirit of the invention.

REFERENCES

The Contents of Which are Incorporated in Full

1. Squinto S P (1996) Xenogeneic organ transplantation. *Curr Opin Biotech* 7: 641-645.
2. McCurry et al. (1996) Human complement regulatory proteins expressed in transgenic swine protect swine xenografts from humoral injury. *Transplant Proc* 28: 758.
3. Dorling et al. (1996). Detection of primary direct and indirect human anti-porcine T cell responses using a porcine dendritic cell population. *Eur J Immunol* 26: 1378-1387.
4. Dorling et al. (1996) Cellular xenoresponses: Although vigorous, direct human T cell anti-pig primary xenoresponses are significantly weaker than equivalent alloresponses. *Xenotransplantation* 3: 149-157.
5. Auchincloss (1995) Why is cell-mediated xenograft rejection so strong? *Xeno* 3: 19.
6. Auchincloss (1988) Xenogeneic transplantation. *Transplantation* 46: 1.
7. Dorling et al. (1996) Cellular xenoresponses: Observation of significant primary indirect human T cell anti-pig xenoresponses using co-stimulator-deficient or SLA class II-negative porcine stimulators. *Xenotransplantation* 3: 112-119.
8. Linsley et al. (1991) CTLA-4 is a second receptor for the B-cell activation antigen B7. *J Exp Med* 174:561-569.
9. Lane et al. (1993) Expression and functional properties of mouse B7/BB1 using a fusion protein between mouse CTLA4 and human γ1. *Immunology* 80: 56.
10. Cohen (1992) Mounting a targeted strike on unwanted immune responses. *Science* 257:751.
11. Baliga et al. (1994) CTLA4Ig prolongs allograft survival while suppressing cell mediated immunity. *Transplantation* 58: 1082-1090.
12. Lenschow et al. (1992) Long term survival of xenogeneic pancreatic islet grafts induced by CTLA4-Ig. *Science* 257: 789-792.

13. Heckl-Östreicher et al. (1995) Functional activity of the membrane-associated complement inhibitor CD59 in a pig-to-human in vitro model for hyperacute xenograft rejection. *Clin. Exp. Immunol.* 102:589-595.
14. McCurry et al. (1996) Human complement regulatory proteins expressed in transgenic swine protect swine xenografts from humoral injury. *Transplant Proc* 28: 758.
15. White et al. (1995) The control of hyperacute rejection by genetic engineering of the donor species. *Eye* 9: 185-189.
16. Yannoutsos et al. (1995) Production of pigs transgenic for human regulators of complement activation. *Transplant Proc* 27: 324-325.
17. Langford et al. (1996) Production of pigs transgenic for human regulators of complement activation using YAC technology. *Transplant Proc* 28: 862-863.
18. Bradley & Liu (1996) Target practice in transgenics. *Nature Genet* 14: 121-123.
19. Clarke (1996) The adenovirus and the egg: a new approach to transgenesis. *Nature Biotech.* 14:942.
20. Wheeler (1994) Development and validation of swine embryonic stem cells: a review. *Reprod Fertil Dev* 6:563-568.
21. Parsons et al. (1996) Cattle CTLA-4, CD28 and chicken CD28 bind CD86: MYPPPY is not conserved in cattle CD28. *Immunogenetics* 43: 388-391.
22. Dorling et al. (1996) In vitro accommodation of immortalized porcine endothelial cells. *Transplantation* 62:1127-1136.
23. Marelli-Berg et al. (1996) Major histocompatibility complex class II-expressing endothelial cells induce allospecific nonresponsiveness in naive T cells. *J Exp Med* 183: 1603.

The invention claimed is:

1. A non-human cell transformed with a vector which expresses a nucleic acid which encodes a porcine CTLA4 protein or fragment thereof.

2. The cell according to claim 1 wherein the CTLA4 protein comprises the extracellular domain of porcine CTLA-4.

3. The cell according to claim 1, wherein the CTLA-4 protein comprises the extracellular domain of porcine CTLA4 fused to a human Cγ1 sequence.

4. The cell of claim 1 wherein the nucleic acid comprises SEQ ID NO: 2.

5. The cell according to claim 1 wherein the CTLA4 protein is fused to the constant domain of an immunoglobulin.

6. The cell of claim 3, wherein the immunoglobulin gamma comprises a constant region of the human Cγ1 subtype.

7. The cell of claim 5, wherein a linker connects the porcine CTLA-4 to the immunoglobulin and the linker comprises the amino acid sequence GGSGGAA (SEQ ID NO: 28).

8. The cell of claim 1 wherein the CTLA-4 protein is fused to an immunoglobulin.

9. The cell of claim 8, wherein the immunoglobulin is a human immunoglobulin.

10. The cell of claim 8, wherein the human immunoglobulin is immunoglobulin gamma (IgG).

11. The cell of claim 10, wherein the immunoglobulin gamma comprises a constant region of the human Cγ1 subtype.

12. The cell of claim 8, wherein a linker connects the porcine CTLA-4 to the immunoglobulin.

13. The cell of claim 12, wherein the linker comprises the amino acid sequence GGSGGAA (SEQ ID NO: 28).

14. The cell of claim 2 wherein the extracellular domain of the porcine CTLA-4 protein comprises amino acid sequence numbers 38-161 of SEQ ID NO: 1.

* * * * *

SEQUENCE LISTING

```
<160> NUMBER OF SEQ ID NOS: 35

<210> SEQ ID NO 1
<211> LENGTH: 223
<212> TYPE: PRT
<213> ORGANISM: Sus scrofa

<400> SEQUENCE: 1

Met Ala Cys Ser Gly Phe Arg Ser His Gly Ala Trp Leu Glu Leu Thr
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala Gln Pro Ala Val Val Leu Ala
        35                  40                  45

Asn Ser Arg Gly Val Ala Ser Phe Val Cys Glu Tyr Gly Ser Ala Gly
    50                  55                  60

Lys Ala Ala Glu Val Arg Val Thr Val Leu Arg Arg Ala Gly Ser Gln
65                  70                  75                  80

Met Thr Glu Val Cys Ala Ala Thr Tyr Thr Val Glu Asp Glu Leu Thr
                85                  90                  95

Phe Leu Asp Asp Ser Thr Cys Thr Gly Thr Ser Thr Glu Asn Lys Val
            100                 105                 110

Asn Leu Thr Ile Gln Gly Leu Arg Ala Val Asp Thr Gly Leu Tyr Ile
        115                 120                 125

Cys Lys Val Glu Leu Leu Tyr Pro Pro Tyr Tyr Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Ile Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 2
<211> LENGTH: 672
<212> TYPE: DNA
<213> ORGANISM: Sus scrofa
```

-continued

```
<400> SEQUENCE: 2
atggcttgct ctggattccg gagccatggg gcttggctgg agcttacttc taggacctgg      60
ccctgtacag ctctgttttc tcttctcttc atccctgtct tctccaaagg gatgcacgtg     120
gcccaacctg cagtagtgct ggccaacagc cggggtgttg ccagctttgt gtgtgagtat     180
gggtctgcag gcaaagctgc cgaggtccgg gtgacagtgc tgcggcgggc cggcagccag     240
atgactgaag tctgtgccgc gacatatact gtggaggatg agttgacctt ccttgatgac     300
tctacatgca ctggcaccctc caccgaaaac aaagtgaacc tcaccatcca agggctgaga    360
gccgtggaca ctgggctcta catctgcaag gtggagctcc tgtacccacc accctactat     420
gtgggtatgg gcaacgggac ccagatttat gtcattgatc cagaaccatg cccagattct     480
gatttcctgc tctggatcct ggcagcagtt agttcaggt tgttttttta cagcttcctc      540
atcacagctg tttctttgag caaaatgcta agaaaagaa gtcctcttac tacaggggtc      600
tatgtgaaaa tgcccccgac agagccagaa tgtgaaaagc aatttcagcc ttatttatt      660 cccatcaatt ga                                                         672

<210> SEQ ID NO 3
<211> LENGTH: 400
<212> TYPE: PRT
<213> ORGANISM: Artificial Sequence
<220> FEATURE:
<223> OTHER INFORMATION: pCTLA4-Ig construct

<400> SEQUENCE: 3

Met Ala Cys Ser Gly Phe Arg Ser His Gly Ala Trp Leu Glu Leu Thr
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala Gln Pro Ala Val Val Leu Ala
        35                  40                  45

Asn Ser Arg Gly Val Ala Ser Phe Val Cys Glu Tyr Gly Ser Ala Gly
    50                  55                  60

Lys Ala Ala Glu Val Arg Val Thr Val Leu Arg Arg Ala Gly Ser Gln
65                  70                  75                  80

Met Thr Glu Val Cys Ala Ala Thr Tyr Thr Val Glu Asp Glu Leu Thr
                85                  90                  95

Phe Leu Asp Asp Ser Thr Cys Thr Gly Thr Ser Thr Glu Asn Lys Val
            100                 105                 110

Asn Leu Thr Ile Gln Gly Leu Arg Ala Val Asp Thr Gly Leu Tyr Ile
        115                 120                 125

Cys Lys Val Glu Leu Leu Tyr Pro Pro Pro Tyr Tyr Val Gly Met Gly
    130                 135                 140

Asn Gly Thr Gln Ile Tyr Val Ile Asp Pro Glu Pro Cys Pro Asp Ser
145                 150                 155                 160

Asp Gly Gly Ser Gly Gly Ala Ala Glu Pro Lys Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
```

```
            225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
                260                 265                 270

Lys Cys Lys Val Ser Asn Lys Ala Leu Pro Ala Pro Ile Glu Lys Thr
                275                 280                 285

Ile Ser Lys Ala Lys Gly Gln Pro Arg Glu Pro Gln Val Tyr Thr Leu
                290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
                355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly Lys
385                 390                 395                 400

<210> SEQ ID NO 4
<211> LENGTH: 722
<212> TYPE: DNA
<213> ORGANISM: Artificial Sequence
<220> FEATURE:
<223> OTHER INFORMATION: phage library

<400> SEQUENCE: 4
ccgaggtgca gctggtggag tctggggggag cttggtaca gcctgggggg tccctgagac    60
tctcctgtgc agcctctgga ttcacctttta gcagctatgc catgagctgg gtccgccagg   120
ctccagggaa ggggctggag tgggtctcag ctattcgtgg tagtggtggt agcacatact   180
acgcagactc cgtgaagggc cggttcacca tctccagaga caattccaag aacacgctgt   240
atctgcaaat gaacagcctg agagccgagg acacggccgt gtattactgt gcaagagctg   300
gtcgtatttt gtttgactat tggggccaag gtacccctggt caccgtctcg agtggtggag   360
gcggttcagg cggaggtggc tctggcggta gtgcacttca gtctgtgctg actcagccac   420
cctcagcgtc tgggaccccc gggcagcggg tcaccatctc ttgttctgga agcagctcca   480
acatcggaag taattatgta tactggtacc agcagctccc aggaacggcc cccaaactcc   540
tcatctatag gaataatcag cggccctcag gggtccctga ccgattctct ggctccaagt   600
ctggcacctc agcctccctg gccatcagtg ggctccggtc cgaggatgag gctgattatt   660
actgtgcagc atgggatgac agcctggtat tcggcggagg gaccaagctc accgtcctag   720
gt                                                                  722

<210> SEQ ID NO 5
<211> LENGTH: 240
<212> TYPE: PRT
<213> ORGANISM: Artificial Sequence
<220> FEATURE:
<223> OTHER INFORMATION: phage library

<400> SEQUENCE: 5

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
                35                  40                  45
Ser Ala Ile Ser Gly Ser Gly Gly Ser Thr Tyr Tyr Ala Asp Ser Val
                50                  55                  60
Lys Gly Arg Phe Thr Ile Ser Arg Asp Asn Ser Lys Asn Thr Leu Tyr
65                              70              75                      80
Leu Gln Met Asn Ser Leu Arg Ala Glu Asp Thr Ala Val Tyr Tyr Cys
                        85                  90                  95
Ala Arg Ala Gly Arg Ile Leu Phe Asp Tyr Trp Gly Gln Gly Thr Leu
                    100                 105                 110
Val Thr Val Ser Ser Gly Gly Gly Gly Ser Gly Gly Gly Gly Ser Gly
                    115                 120                 125
Gly Ser Ala Leu Gln Ser Val Leu Thr Gln Pro Pro Ser Ala Ser Gly
                    130                 135                 140
Thr Pro Gly Gln Arg Val Thr Ile Ser Cys Ser Gly Ser Ser Ser Asn
145                 150                 155                     160
Ile Gly Ser Asn Tyr Val Tyr Trp Tyr Gln Gln Leu Pro Gly Thr Ala
                    165                 170                 175
Pro Lys Leu Leu Ile Tyr Arg Asn Asn Gln Arg Pro Ser Gly Val Pro
                    180                 185                 190
Asp Arg Phe Ser Gly Ser Lys Ser Gly Thr Ser Ala Ser Leu Ala Ile
                    195                 200                 205
Ser Gly Leu Arg Ser Glu Asp Glu Ala Asp Tyr Tyr Cys Ala Ala Trp
                    210                 215                 220
Asp Asp Ser Leu Val Phe Gly Gly Gly Thr Lys Leu Thr Val Leu Gly
225                 230                 235                     240

<210> SEQ ID NO 6
<211> LENGTH: 729
<212> TYPE: DNA
<213> ORGANISM: Artificial Sequence
<220> FEATURE:
<223> OTHER INFORMATION: phage library

<400> SEQUENCE: 6
catggccgag gtgcagctgg tggagtctgg gggaggcttg gtacagcctg gggggtccct    60
gagactctcc tgtgcagcct ctggattcac ctttagcagc tatgccatga gctgggtccg   120
ccaggctcca gggaaggggc tggagtgggt ctcagctatt agtggtagtg gtggtagcac   180
atactacgca gactccgtga agggccggtt caccatctcc agagacaatt ccaagaacac   240
gctgtatctg caaatgaaca gcctgagagc cgaggacacg gccgtgtatt actgtgcaag   300
agctggtcgt atttttgttt actattgggg ccaaggtacc ctggtcaccg tctcgagtgg   360
tggaggcggt tcaggcggag gtggctctgg cggtagtgca cttcagtctg tgctgactca   420
gccacccctca gcgtctggga ccccgggca gagggtcacc atctcttgtt ctggaagcag   480
ctccaacatc ggaagtaatt atgtatactg gtaccagcag ctcccaggaa cggcccccaa   540
actcctcatc tataggaata atcagcggcc ctcagggtc cctgaccgat tctctggctc   600
caagtctggc acctcagcct ccctggccat cagtgggctc cggtccgagg atgaggctga   660
ttattactgt gcagcatggg atgacagcct ggtattcggc ggagggacca agctgaccgt   720
cctaggtgc                                                          729
```

<210> SEQ ID NO 7
<211> LENGTH: 738
<212> TYPE: DNA
<213> ORGANISM: Artificial Sequence
<220> FEATURE:
<223> OTHER INFORMATION: phage library

<400> SEQUENCE: 7

| | | | | | |
|---|---|---|---|---|---|
| catggccgag | gtgcagctgc | aggagtcggg | cccaggactg | gtgaagcctc | gggagaccct | 60 |
| gtccctcacc | tgcactgtct | ctggtggctc | cgtcagcagt | ggtagttact | ggagctggat | 120 |
| ccggcagccc | ccagggaagg | gactggagtg | gattgggtat | atctattaca | gtgggagcac | 180 |
| caactacaac | ccctccctca | agagtcgagt | caccatatca | gtagacacgt | ccaagaacca | 240 |
| gttctccctg | aagctgagct | ctgtgaccgc | tgcggacacg | gccgtgtatt | actgtgcaag | 300 |
| aatgcggaag | ataagtttg  | actattgggg | ccaaggtacc | ctggtcaccg | tctcgagtgg | 360 |
| tggaggcggt | tcaggcggag | gtggctctgg | cggtagtgca | cttcagtctg | tgctgactca | 420 |
| gccaccctca | gcgtctggga | cccccgggca | gagggtcacc | atctcttgtt | ctggaagcag | 480 |
| ctccaacatc | ggaagtaatt | atgtatactg | gtaccagcag | ctcccaggaa | cggcccccaa | 540 |
| actcctcatc | tataggaata | atcagcggcc | ctcagggtc  | cctgaccgat | tctctggctc | 600 |
| caagtctggc | acctcagcct | ccctggccat | cagtgggctc | cggtccgagg | atgaggctga | 660 |
| ttattactgt | gcagcatggg | atgacagcct | gtttgtattc | ggcggaggga | ccaagctgac | 720 |
| cgtcctaggt | gcggccgc | | | | | 738 |

<210> SEQ ID NO 8
<211> LENGTH: 735
<212> TYPE: DNA
<213> ORGANISM: Artificial Sequence
<220> FEATURE:
<223> OTHER INFORMATION: phage library

<400> SEQUENCE: 8

| | | | | | |
|---|---|---|---|---|---|
| catggcccag | gtgcagctgg | tgcagtctgg | ggctgaggtg | aagaggcctg | gggcctcagt | 60 |
| gaaggtttcc | tgcaaggcat | ctggatacac | cttcaccagc | tactatatgc | actgggtgcg | 120 |
| acaggcccct | ggacaagggc | ttgagtggat | gggaataatc | aaccctagtg | gtggtagcac | 180 |
| aagctacgca | cagaagttcc | agggcagagt | caccatgacc | agggacacgt | ccacgagcac | 240 |
| agtctacatg | gagctgagca | gcctgagatc | tgaggacacg | gccgtgtatt | actgtgcaag | 300 |
| agtggctccc | tatgtgaata | cgcttgtttt | ttggggccaa | ggtaccctgg | tcaccgtctc | 360 |
| gagtggtgga | ggcggttcag | gcggaggtgg | ctctggcggt | agtgcacttt | cttctgagct | 420 |
| gactcaggac | cctgctgtgt | ctgtggcctt | gggacagaca | gtcaggatca | catgccaagg | 480 |
| agacagcctc | agaagctatt | atgcaagctg | gtaccagcag | aagccaggac | aggcccctgt | 540 |
| acttgtcatc | tatggtaaaa | acaaccggcc | ctcaggatc  | ccagaccgat | tctctggctc | 600 |
| cagctcagga | aacacagctt | ccttgaccat | cactgggct  | caggcggaag | atgaggctga | 660 |
| ctattactgt | aactcccggg | acagcagtgg | ttttactgta | ttcggcggag | ggaccaagct | 720 |
| gaccgtccta | ggtgc | | | | | 735 |

<210> SEQ ID NO 9
<211> LENGTH: 729
<212> TYPE: DNA
<213> ORGANISM: Artificial Sequence
<220> FEATURE:

<223> OTHER INFORMATION: phage library

<400> SEQUENCE: 9

```
catgggccca ggtgcagctg ttgcagtctg cagcagaggt gaaaaagccc ggggagtctc    60
tgaagatctc ctgtaagggt tctggataca gctttaccag ctactggatc ggctgggtgc   120
gccagatgcc cgggaaaggc ctggagtgga tggggatcat ctatcctggt gactctgata   180
ccagatacag cccgtccttc caaggccagg tcaccatctc agccgacaag tccatcagca   240
ccgcctacct gcagtggagc agcctgaagg cctcggacac ggccgtgtat tactgtgcaa   300
gattttcgct tggtggtttt gactattggg gccaaggtac cctggtcacc gtctcgagtg   360
gtggaggcgg ttcaggcgga ggtggctctg gcggtagtgc acttgacatc cagttgaccc   420
agtctccatg ttcctgtctg catctgtagg agacagagtc accatcactt gccgggccag   480
tcagggcatt agcagttatt tagcctggta tcagcaaaaa ccagggaaag cccctaagct   540
cctggtctat gctgcatcca ctttgcaaag tggggtccca tcaaggttca gcggcagtgg   600
atctgggaca gaattcactc tcacaatcag cagcctgcag cctgaagatt ttgcaactta   660
ttactgtcaa cagcttaata gttaccgctt gacgttcggc caagggacca gctggaaat   720
caaacgtgc                                                           729
```

<210> SEQ ID NO 10
<211> LENGTH: 240
<212> TYPE: PRT
<213> ORGANISM: Artificial Sequence
<220> FEATURE:
<223> OTHER INFORMATION: phage library

<400> SEQUENCE: 10

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Arg Ile Leu Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Ser Ala Leu Gln Ser Val Leu Thr Gln Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Ser Asn Tyr Val Tyr Trp Tyr Gln Gln Leu Pro Gly Thr Ala
                165                 170                 175

Pro Lys Leu Leu Ile Tyr Arg Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205
```

```
Ser Gly Leu Arg Ser Glu Asp Glu Ala Ser Tyr Tyr Cys Ala Ala Trp
    210                 215                 220

Asp Asp Ser Leu Val Phe Gly Gly Gly Thr Lys Leu Thr Val Leu Gly
225                 230                 235                 240
```

<210> SEQ ID NO 11
<211> LENGTH: 246
<212> TYPE: PRT
<213> ORGANISM: Artificial Sequence
<220> FEATURE:
<223> OTHER INFORMATION: phage library

<400> SEQUENCE: 11

```
Met Ala Gln Val Gln Leu Gln Glu Ser Gly Pro Gly Leu Val Lys Pro
1               5                   10                  15

Ser Glu Thr Leu Ser Leu Thr Cys Thr Val Ser Gly Gly Ser Val Ser
            20                  25                  30

Ser Gly Ser Tyr Tyr Trp Ser Trp Ile Arg Gln Pro Pro Gly Lys Gly
        35                  40                  45

Leu Glu Trp Ile Gly Tyr Ile Tyr Tyr Ser Gly Ser Thr Asn Tyr Asn
    50                  55                  60

Pro Ser Leu Lys Ser Arg Val Thr Ile Ser Val Asp Thr Ser Lys Asn
65                  70                  75                  80

Gln Phe Ser Leu Lys Leu Ser Ser Val Thr Ala Ala Asp Thr Ala Val
                85                  90                  95

Tyr Tyr Cys Ala Arg Met Arg Lys Asp Lys Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Ser Ala Leu Gln Ser Val Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Ile Gly Ser Asn Tyr Val Tyr Trp Tyr Gln Gln Leu Pro
                165                 170                 175

Gly Thr Ala Pro Lys Leu Leu Ile Tyr Arg Asn Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Val
    210                 215                 220

Ala Ala Trp Asp Asp Ser Leu Phe Val Phe Gly Gly Gly Thr Lys Leu
225                 230                 235                 240

Thr Val Leu Gly Ala Ala
                245
```

<210> SEQ ID NO 12
<211> LENGTH: 242
<212> TYPE: PRT
<213> ORGANISM: Artificial Sequence
<220> FEATURE:
<223> OTHER INFORMATION: phage library

<400> SEQUENCE: 12

```
Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ala Pro Tyr Val Asn Thr Leu Val Phe Trp Gly Gln Gly
                100                 105                 110

Thr Leu Val Thr Val Ser Gly Gly Gly Ser Gly Gly Gly
                115                 120                 125

Ser Gly Gly Ser Ala Leu Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
                180                 185                 190

Asp Arg Phe Ser Gly Ser Ser Ser Gly Asn Thr Ala Ser Leu Thr Ile
                195                 200                 205

Thr Gly Ala Gln Ala Glu Asp Glu Ala Asp Tyr Tyr Cys Asn Ser Arg
    210                 215                 220

Asp Ser Ser Gly Phe Thr Val Phe Gly Gly Thr Lys Leu Thr Val
225                 230                 235                 240

Leu Gly

<210> SEQ ID NO 13
<211> LENGTH: 240
<212> TYPE: PRT
<213> ORGANISM: Artificial Sequence
<220> FEATURE:
<223> OTHER INFORMATION: phage library

<400> SEQUENCE: 13

Gln Val Gln Leu Leu Gln Ser Ala Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Phe Ser Leu Gly Gly Phe Asp Tyr Trp Gly Gln Gly Thr Leu
                100                 105                 110

Val Thr Val Ser Ser Gly Gly Gly Gly Ser Gly Gly Gly Gly Ser Gly
            115                 120                 125

Gly Ser Ala Leu Asp Ile Gln Leu Thr Gln Ser Pro Ser Phe Leu Ser
    130                 135                 140
```

```
Ala Ser Val Gly Asp Arg Val Thr Ile Thr Cys Arg Ala Ser Gln Gly
145                 150                 155                 160

Ile Ser Ser Tyr Leu Ala Trp Tyr Gln Gln Lys Pro Gly Lys Ala Pro
            165                 170                 175

Lys Leu Leu Val Tyr Ala Ala Ser Thr Leu Gln Ser Gly Val Pro Ser
        180                 185                 190

Arg Phe Ser Gly Ser Gly Ser Gly Thr Glu Phe Thr Leu Thr Ile Ser
    195                 200                 205

Ser Leu Gln Pro Glu Asp Phe Ala Thr Tyr Tyr Cys Gln Gln Leu Asn
        210                 215                 220

Ser Tyr Arg Leu Thr Phe Gly Gln Gly Thr Lys Leu Glu Ile Lys Arg
225             230                 235                 240

<210> SEQ ID NO 14
<211> LENGTH: 742
<212> TYPE: DNA
<213> ORGANISM: Homo sapiens

<400> SEQUENCE: 14
agcttcagga tcctgaaagg ttttgctcta cttcctgaag acctgaacac cgctcccata    60
aagccatggc ttgccttgga tttcagcggc acaaggctca gctgaacctg gctaccagga   120
cctggccctg cactctcctg ttttttcttc tcttcatccc tgtcttctgc aaagcaatgc   180
acgtggccca gctgctgtg gtactggcca gcagccgagg catcgccagc tttgtgtgtg   240
agtatgcatc tccaggcaaa gccactgagg tccgggtgac agtgcttcgg caggctgaca   300
gccaggtgac tgaagtctgt gcggcaacct acatgatggg gaatgagttg accttcctag   360
atgattccat ctgcacgggc acctccagtg gaaatcaagt gaacctcact atccaaggac   420
tgagggccat ggacacggga ctctacatct gcaaggtgga gctcatgtac ccaccgccat   480
actacctggg cataggcaac ggaacccaga tttatgtaat tgatccagaa ccgtgcccag   540
attctgactt cctcctctgg atccttgcag cagttagttc gggggttgttt ttttatagct   600
ttctcctcac agctgtttct tgagcaaaaa tgctaaagaa aagaagccct cttacaacag   660
gggtctatgt gaaaatgccc ccaacagagc cagaatgtga aaagcaattt cagccttatt   720
ttattcccat caattgagaa tt                                            742

<210> SEQ ID NO 15
<211> LENGTH: 223
<212> TYPE: PRT
<213> ORGANISM: Homo sapiens

<400> SEQUENCE: 15

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
```

```
              100                 105                 110
Asn Leu Thr Ile Gln Gly Leu Arg Ala Met Asp Thr Gly Leu Tyr Ile
            115                 120                 125

Cys Lys Val Glu Leu Met Tyr Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
        210                 215                 220
```

<210> SEQ ID NO 16
<211> LENGTH: 773
<212> TYPE: DNA
<213> ORGANISM: Homo sapiens

<400> SEQUENCE: 16

| | | | | | |
|---|---|---|---|---|---|
| aagcttcgag | ccaagcagcg | tcctggggag | cgcgtcatgg | ccttaccagt | gaccgccttg | 60 |
| ctcctgccgc | tggccttgct | gctccacgcc | gccaggccga | gccagttccg | ggtgtcgccg | 120 |
| ctggatcgga | cctggaacct | gggcgagaca | gtggagctga | agtgccaggt | gctgctgtcc | 180 |
| aacccgacgt | cgggctgctc | gtggctcttc | cagccgcgcg | gcgccgccgc | cagtcccacc | 240 |
| ttcctcctat | acctctccca | aaacaagccc | aaggcggccg | aggggctgga | cacccagcgg | 300 |
| ttctcgggca | gaggttgggg | ggacaccttc | gtcctcaccc | tgagcgactt | ccgccgagag | 360 |
| aacgagggct | actatttctg | ctcggccctg | agcaactcca | tcatgtactt | cagccacttc | 420 |
| gtgccggtct | tcctgccagc | gaagcccacc | acgacgccag | cgccgcgacc | accaacaccg | 480 |
| gcgcccacca | tcgcgtcgca | gccccctgtc | ctgcgcccag | aggcgtgccg | gccagcggcg | 540 |
| ggggcgcag | tgcacacgag | ggggctggac | ttcgcctgtg | atatctacat | ctgggcgccc | 600 |
| ttggccggga | cttgtggggt | ccttctcctg | tcactggtta | tcacccttta | ctgcaaccac | 660 |
| aggaaccgaa | gacgtgtttg | caaatgtccc | cggcctgtgg | tcaaatcggg | agacaagccc | 720 |
| agcctttcgg | cgagatacgt | ctaaccctgt | gcaacagcca | ctacatgaat | tcc | 773 |

<210> SEQ ID NO 17
<211> LENGTH: 28
<212> TYPE: DNA
<213> ORGANISM: Artificial Sequence
<220> FEATURE:
<223> OTHER INFORMATION: sythetic primer

<400> SEQUENCE: 17
ttgaagctta gccatggctt gctctgga                                    28

<210> SEQ ID NO 18
<211> LENGTH: 33
<212> TYPE: DNA
<213> ORGANISM: Artificial Sequence
<220> FEATURE:
<223> OTHER INFORMATION: synthetic primer

<400> SEQUENCE: 18

```
taatgaattc tcaattgatg ggaataaaat aag                              33

<210> SEQ ID NO 19
<211> LENGTH: 60
<212> TYPE: DNA
<213> ORGANISM: Artificial Sequence
<220> FEATURE:
<223> OTHER INFORMATION: synthetic primer

<400> SEQUENCE: 19
cggttctgca gcaccaccgg agccaccatc agaatctggg catggttctg gatcaatgac    60

<210> SEQ ID NO 20
<211> LENGTH: 25
<212> TYPE: DNA
<213> ORGANISM: Artificial Sequence
<220> FEATURE:
<223> OTHER INFORMATION: synthetic primer

<400> SEQUENCE: 20
gagctgaaac gggcggccgc agaac                                       25

<210> SEQ ID NO 21
<211> LENGTH: 22
<212> TYPE: DNA
<213> ORGANISM: Artificial Sequence
<220> FEATURE:
<223> OTHER INFORMATION: synthetic primer

<400> SEQUENCE: 21
ctggcctgca gcattcagat cc                                          22

<210> SEQ ID NO 22
<211> LENGTH: 30
<212> TYPE: DNA
<213> ORGANISM: Artificial Sequence
<220> FEATURE:
<223> OTHER INFORMATION: synthetic primer

<400> SEQUENCE: 22
ttcaaagctt caggatcctg aaaggttttg                                  30

<210> SEQ ID NO 23
<211> LENGTH: 33
<212> TYPE: DNA
<213> ORGANISM: Artificial Sequence
<220> FEATURE:
<223> OTHER INFORMATION: synthetic primer

<400> SEQUENCE: 23
taatgaattc tcaattgatg ggaataaaat aag                              33

<210> SEQ ID NO 24
<211> LENGTH: 76
<212> TYPE: DNA
<213> ORGANISM: Artificial Sequence
<220> FEATURE:
<223> OTHER INFORMATION: synthetic primer

<400> SEQUENCE: 24
gatgtagata tcacaggcga agtcgacacc accggagcca ccaattacat aaatctgggc    60
tccgttgcct atgccc                                                 76

<210> SEQ ID NO 25
<211> LENGTH: 29
```

```
<212> TYPE: DNA
<213> ORGANISM: Artificial Sequence
<220> FEATURE:
<223> OTHER INFORMATION: synthetic primer

<400> SEQUENCE: 25
tcgcgcccaa gcttcgagcc aagcagcgt                              29

<210> SEQ ID NO 26
<211> LENGTH: 33
<212> TYPE: DNA
<213> ORGANISM: Artificial Sequence
<220> FEATURE:
<223> OTHER INFORMATION: synthetic primer

<400> SEQUENCE: 26
taatgaattc tcaattgatg ggaataaaat aag                         33

<210> SEQ ID NO 27
<211> LENGTH: 73
<212> TYPE: DNA
<213> ORGANISM: Artificial Sequence
<220> FEATURE:
<223> OTHER INFORMATION: synthetic primer

<400> SEQUENCE: 27
cataggcaac ggagcccaga tttatgtaat tggtggctcc ggtggtgtcg acttcgcctg    60
tgatatctac atc                                              73

<210> SEQ ID NO 28
<211> LENGTH: 7
<212> TYPE: PRT
<213> ORGANISM: Artificial Sequence
<220> FEATURE:
<223> OTHER INFORMATION: synthetic linker

<400> SEQUENCE: 28

Gly Gly Ser Gly Gly Ala Ala
1               5

<210> SEQ ID NO 29
<211> LENGTH: 6
<212> TYPE: PRT
<213> ORGANISM: Artificial Sequence
<220> FEATURE:
<223> OTHER INFORMATION: hexapeptide motif

<400> SEQUENCE: 29

Met Tyr Pro Pro Pro Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: hexapeptide linker

<400> SEQUENCE: 30

Leu Tyr Pro Pro Pro Tyr
1               5

<210> SEQ ID NO 31
<211> LENGTH: 223
<212> TYPE: PRT
<213> ORGANISM: Homo sapiens
```

<400> SEQUENCE: 31

```
Met Ala Cys Leu Gly Phe Gln Arg His Lys Ala Gln Leu Asn Leu Ala
1               5                   10                  15

Ala Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
130                 135                 140

Asn Gly Ala Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 32
<211> LENGTH: 221
<212> TYPE: PRT
<213> ORGANISM: Bos taurus

<400> SEQUENCE: 32

```
Met Ala Cys Ser Gly Phe Gln Ser His Gly Thr Trp Trp Thr Ser Arg
1               5                   10                  15

Thr Trp Pro Cys Thr Ala Leu Phe Phe Leu Val Phe Ile Pro Val Phe
            20                  25                  30

Ser Lys Gly Met Asn Val Thr Gln Pro Pro Val Val Leu Ala Ser Ser
        35                  40                  45

Arg Gly Val Ala Ser Phe Ser Cys Glu Tyr Glu Ser Ser Gly Lys Ala
    50                  55                  60

Asp Glu Val Arg Val Thr Val Leu Arg Glu Ala Gly Ser Gln Val Thr
65                  70                  75                  80

Glu Val Cys Ala Gly Thr Tyr Met Val Glu Asp Glu Leu Thr Phe Leu
                85                  90                  95

Asp Asp Ser Thr Cys Ile Gly Thr Ser Arg Gly Asn Lys Val Asn Leu
            100                 105                 110

Thr Ile Gln Gly Leu Arg Ala Met Asp Thr Gly Leu Tyr Val Cys Lys
        115                 120                 125

Val Glu Leu Met Tyr Pro Pro Pro Tyr Tyr Val Gly Ile Gly Asn Gly
130                 135                 140
```

```
Thr Gln Ile Tyr Val Ile Asp Pro Glu Pro Cys Pro Asp Ser Asp Phe
145                 150                 155                 160

Leu Leu Trp Ile Leu Ala Ala Val Ser Ser Gly Leu Phe Phe Tyr Ser
                165                 170                 175

Phe Leu Ile Thr Ala Val Ser Leu Ser Lys Met Leu Lys Lys Arg Ser
            180                 185                 190

Pro Leu Thr Thr Gly Val Tyr Val Lys Met Pro Pro Thr Glu Pro Glu
        195                 200                 205

Cys Glu Lys Gln Phe Gln Pro Tyr Phe Ile Pro Ile Asn
    210                 215                 220
```

<210> SEQ ID NO 33
<211> LENGTH: 672
<212> TYPE: DNA
<213> ORGANISM: Homo sapiens

<400> SEQUENCE: 33

```
atggcttgcc ttggatttca gcggcacaag gctcagctga acctggctgc caggacctgg      60
ccctgcactc tcctgttttt tcttctcttc atccctgtct tctgcaaagc aatgcacgtg     120
gcccagcctg ctgtggtact ggccagcagc cgaggcatcg ccagctttgt gtgtgagtat     180
gcatctccag gcaaagccac tgaggtccgg gtgacagtgc ttcggcaggc tgacagccag     240
gtgactgaag tctgtgcggc aacctacatg atggggaatg agttgacctt cctagatgat     300
tccatctgca ccggcaccct cagtggaaat caagtgaacc tcactatcca aggactgagg     360
gccatggaca cgggactcta catctgcaag gtggagctca tgtacccacc gccatactac     420
ctgggcatag gcaacggagc ccagatttat gtaattgatc cagaaccgtg cccagattct     480
gacttcctcc tctggatcct tgcagcagtt agttcgggtc tgttttttta tagctttctc     540
ctcacagctg tttctttgag caaaatgcta aagaaagaa gccctcttac aacagggtc     600
tatgtgaaaa tgcccccaac agagccagaa tgtgaaaagc aatttcagcc ttatttttatt     660
cccatcaatt ga                                                          672
```

<210> SEQ ID NO 34
<211> LENGTH: 666
<212> TYPE: DNA
<213> ORGANISM: Bos taurus

<400> SEQUENCE: 34

```
atggcttgct ctggattcca gagtcatggg acttggtgga catctaggac ctggccctgc      60
actgccctat tttttcttgt cttcatccct gttttctcta aagggatgaa tgtgacccag     120
cctccagtgg tgctggctag cagccggggt gttgccagct tctcatgtga atatgagtct     180
tcaggcaaag ctgacgaggt ccgggtgaca gtgctgcggg aggcaggcag ccaggtgacc     240
gaagtctgtg ctgggaccta catggtggag atgagctaa ccttcctgga tgattccact     300
tgcattggca cctccagagg aaacaaagtg aacctcacca tccaagggct gagggccatg     360
gacactgggc tctatgtctg caaagtggag ctcatgtacc cgccgcccta ctacgtgggc     420
atcggcaatg aacccagat ttacgtcatt gatccagaac catgcccgga ttctgatttt     480
ctcctctgga tcctggcagc agttagttca gggttgtttt tctacagctt cctcatcaca     540
gctgtttctt tgagcaaaat gctaaagaaa agaagccctc ttactacagg ggtctatgtg     600
aaaatgcccc caacagagcc agaatgtgaa agcaatttc agccttattt tattcccatc     660
aattga                                                                666
```

```
<210> SEQ ID NO 35
<211> LENGTH: 5
<212> TYPE: PRT
<213> ORGANISM: Artificial Sequence
<220> FEATURE:
<223> OTHER INFORMATION: synthetic linker

<400> SEQUENCE: 35

Gly Gly Ser Gly Gly
1               5
```